US012383351B2

(12) United States Patent
Freiin von Kapri et al.

(10) Patent No.: US 12,383,351 B2
(45) Date of Patent: *Aug. 12, 2025

(54) TRAINING AND FEEDBACK FOR A CONTROLLER WORKSPACE BOUNDARY

(71) Applicant: Verb Surgical Inc., Santa Clara, CA (US)

(72) Inventors: Anette Lia Freiin von Kapri, Mountain View, CA (US); Eric Mark Johnson, Mountain View, CA (US); Joan Savall, Palo Alto, CA (US)

(73) Assignee: Verb Surgical Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/442,253

(22) Filed: Feb. 15, 2024

(65) Prior Publication Data
US 2024/0268900 A1 Aug. 15, 2024

Related U.S. Application Data

(63) Continuation of application No. 16/833,275, filed on Mar. 27, 2020, now Pat. No. 11,911,120.

(51) Int. Cl.
A61B 34/00 (2016.01)
A61B 34/20 (2016.01)
(Continued)

(52) U.S. Cl.
CPC .............. *A61B 34/25* (2016.02); *A61B 34/20* (2016.02); *A61B 34/37* (2016.02); *A61B 34/76* (2016.02);
(Continued)

(58) Field of Classification Search
CPC ......... A61B 34/25; A61B 34/20; A61B 34/37; A61B 34/76; A61B 2034/2051;
(Continued)

(56) References Cited

U.S. PATENT DOCUMENTS 7,805,269 B2   9/2010   Glossop
8,303,575 B2   11/2012  Rodriguez Y Baena
(Continued)

FOREIGN PATENT DOCUMENTS

CN     108648548 A    10/2018
WO     2018/218175 A1 11/2018
(Continued)

OTHER PUBLICATIONS

Non-Final Office Action received for U.S. Appl. No. 16/833,275, mailed on Sep. 21, 2023, 10 pages.
(Continued)

*Primary Examiner* — Aaron F Roane
(74) *Attorney, Agent, or Firm* — Aikin & Gallant, LLP

(57) ABSTRACT

A method of determining a location of a user input device of a surgical robotic system within a surgical workspace using a virtual workspace including determining, by one or more processors communicatively coupled to a user input device, that a user is engaging with the user input device within a surgical workspace; in response to determining the user is engaging with the user input device, displaying a virtual user input device within a first virtual workspace boundary, wherein at least a portion of the first virtual workspace boundary is operable to move in response to a movement of the user input device; displaying a second virtual workspace boundary that represents a second workspace limit beyond which the user input device is inoperable to control the surgical robotic instrument in the teleoperation mode; and determining a location of the user input device within the surgical workspace.

20 Claims, 25 Drawing Sheets

(51) Int. Cl.
*A61B 34/37* (2016.01)
*A61B 17/00* (2006.01)

(52) U.S. Cl.
CPC ............... *A61B 2017/00115* (2013.01); *A61B 2017/00734* (2013.01); *A61B 2034/2051* (2016.02); *A61B 2034/2055* (2016.02)

(58) Field of Classification Search
CPC .. A61B 2034/2055; A61B 2017/00115; A61B 2017/00734
USPC ............................................................ 606/1
See application file for complete search history.

(56) References Cited

U.S. PATENT DOCUMENTS

| | | | |
|---|---|---|---|
| 8,382,485 B2 | 2/2013 | Bardsley et al. | |
| 8,600,551 B2 | 12/2013 | Itkowitz et al. | |
| 8,831,782 B2 | 9/2014 | Itkowitz | |
| 9,010,214 B2 | 4/2015 | Markvicka et al. | |
| 9,082,319 B2 | 7/2015 | Shimada et al. | |
| 9,283,048 B2 | 3/2016 | Kostrzewski et al. | |
| 9,566,709 B2 | 2/2017 | Kwon et al. | |
| 9,595,207 B2 | 3/2017 | Kesavadas et al. | |
| 9,595,208 B2 | 3/2017 | Ottensmeyer et al. | |
| 9,603,668 B2 | 3/2017 | Weingarten et al. | |
| 10,231,790 B2 | 3/2019 | Quaid et al. | |
| 10,398,520 B2 | 9/2019 | Larkin et al. | |
| 2004/0115606 A1* | 6/2004 | Davies ............... A63B 69/0057 434/258 |
| 2004/0234933 A1 | 11/2004 | Dawson et al. | |
| 2009/0305210 A1 | 12/2009 | Guru et al. | |
| 2017/0249872 A1 | 8/2017 | Piron et al. | |
| 2018/0036088 A1 | 2/2018 | Kilroy et al. | |
| 2018/0153632 A1 | 6/2018 | Tokarchuk et al. | |
| 2018/0293697 A1 | 10/2018 | Ray et al. | |
| 2018/0297206 A1 | 10/2018 | Larkin et al. | |
| 2018/0353254 A1* | 12/2018 | Lutzow .................. A61B 34/25 |
| 2019/0029757 A1 | 1/2019 | Roh et al. | |
| 2019/0090969 A1 | 3/2019 | Jarc et al. | |
| 2019/0213775 A1 | 7/2019 | Dimitrov et al. | |
| 2021/0038335 A1* | 2/2021 | Maret .................... A61B 34/74 |
| 2021/0275264 A1* | 9/2021 | Johnson ................. G16H 30/20 |

FOREIGN PATENT DOCUMENTS

| | | |
|---|---|---|
| WO | 2019/099504 A1 | 5/2019 |
| WO | 2019/099584 A1 | 5/2019 |

OTHER PUBLICATIONS

Notice of Allowance received for U.S. Appl. No. 16/833,275, mailed on Dec. 28, 2023, 7 pages.

Requirement for Restriction/Election received for U.S. Appl. No. 16/833,275, mailed on Aug. 11, 2022, 6 pages.

Requirement for Restriction/Election received for U.S. Appl. No. 16/833,275, mailed on Feb. 3, 2023, 7 pages.

* cited by examiner

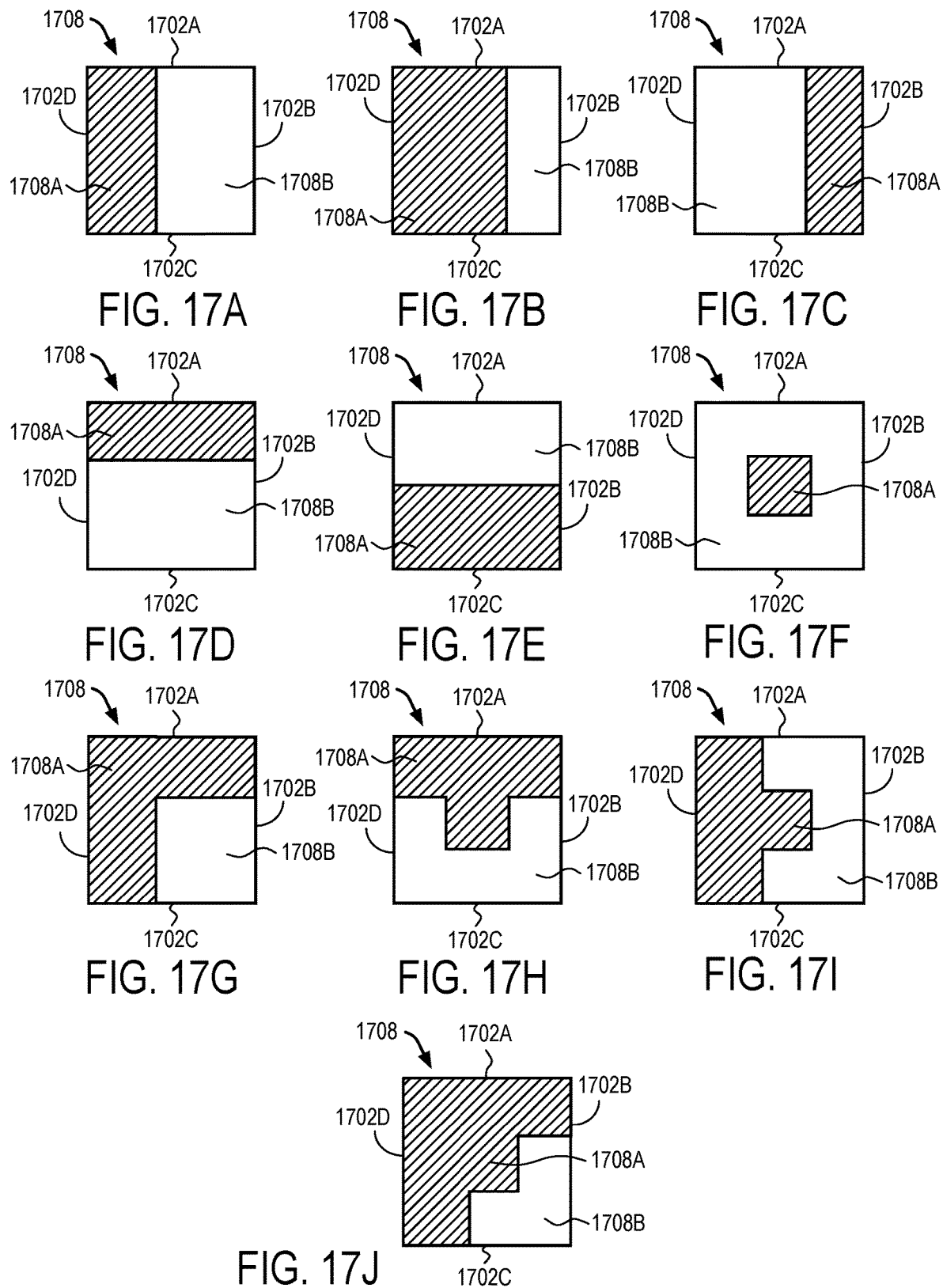

TRAINING AND FEEDBACK FOR A CONTROLLER WORKSPACE BOUNDARY

CROSS-REFERENCE TO RELATED APPLICATIONS

This application is a continuation of U.S. patent application Ser. No. 16/833,275, filed Mar. 27, 2020, entitled "TRAINING AND FEEDBACK FOR A CONTROLLER WORKSPACE BOUNDARY," expected to issue as U.S. Pat. No. 11,911,120, on Feb. 27, 2024, which is hereby incorporated by reference in its entirety.

BACKGROUND

Field

Embodiments related surgical robotic systems, are disclosed. More particularly, embodiments related to training and feedback for a user operating an ungrounded controller in an invisible workspace, are disclosed.

Background

Minimally-invasive surgery (MIS), such as endoscopic surgery, involves looking into a patient's body and performing surgery inside the body using endoscopes and other surgical tools. For example, laparoscopic surgery can use a laparoscope to access and view an abdominal cavity. Endoscopic surgery can be performed using manual tools and/or a surgical robotic system having robotically-assisted tools.

A surgical robotic system may be remotely operated by a surgeon to command a robotically-assisted tool located at an operating table. Such operation of a robotically-assisted tool remotely by a surgeon may be commonly referred to as teleoperation. For example, the surgeon may use a computer console located in the operating room, or it may be located in a different city, to command a robot to manipulate the surgical tool mounted on the operating table. The robotically-controlled surgical tool can be an endoscope mounted on a robotic arm. Accordingly, the surgical robotic system may be used by the remote surgeon to perform an endoscopic surgery.

The surgeon may provide input commands to the surgical robotic system, and one or more processors of the surgical robotic system can control system components in response to the input commands. For example, the surgeon may hold in her hand a user input device that she manipulates to generate control signals to cause motion of the surgical robotic system components, e.g., an actuator, a robotic arm, and/or a surgical tool of the robotic system.

SUMMARY

In some aspects, the surgical robotic system components may be controlled using a user input device or controller that is ungrounded. In the case of ungrounded controllers, which are only usable within a defined workspace area, the user may need training before usage and feedback during usage to ensure the controllers are being used within an operable range. For example, since the ungrounded (e.g., mid-air) controllers have an invisible workspace the user needs to learn in what space she or he can use the controllers and in what space the controllers are inactive. Therefore, in one aspect, the instant disclosure is directed to different multimodal methods for training the user so that they can build a mental model of where they are allowed to move the controllers to. Different multimodal approaches are also provided to give real-time feedback during usage which will prevent the user from going out of the workspace.

Representatively, in one aspect, a multimodal process may include three categories: (1) Training, (2) Pre-Usage Reminder and (3) Feedback During Usage. For the Training, there may be a task that is specifically designed to learn the boundary of the workspace area. For example, there could be a display which shows an outer box representing the actual controller workspace, an inner box representing a warning zone, and spheres representing the controllers within the inner box. If the user moves the controllers into the warning zone, the inner box is shown pushed out and turns a different color to warn the user they may be reaching the workspace limit. If the user reaches the outer box with the controllers, the outer box may turn red and an alarm may sound. The user will be able to fully focus on this one task which will allow her to create a mental model of the workspace. As a Pre-Usage Reminder, the user may perform a quick task during a login sequence to set her or his mind back to the workable area. For the Feedback During Usage there may be GUI and multimodal feedback in a non-intrusive way to inform the user that she or he is approaching the workspace limit (e.g., warning displayed next to the screen). The feedback may be seen in the periphery without interfering with the task at hand. For the sake of simplicity, a box-shaped workspace may be assumed, but these concepts can be expanded to differently shaped workspaces such as a sphere or ellipsoid or any type of three-dimensional (3D) shape.

Representatively, in one aspect, a method of determining a location of a user input device of a surgical robotic system within a surgical workspace using a virtual workspace includes determining, by one or more processors communicatively coupled to a user input device, that a user is engaging with the user input device within a surgical workspace; in response to determining the user is engaging with the user input device, displaying a virtual user input device within a first virtual workspace boundary, the first virtual workspace boundary representing a first workspace limit within which the user input device is operable to control a surgical robotic instrument in a teleoperation mode, wherein at least a portion of the first virtual workspace boundary is operable to move in response to a movement of the user input device; displaying a second virtual workspace boundary that represents a second workspace limit beyond which the user input device is inoperable to control the surgical robotic instrument in the teleoperation mode; and determining, by one or more processors, a location of the user input device within the surgical workspace based on a proximity of the portion of the first virtual workspace boundary relative to the second virtual workspace boundary. In some aspects, the first virtual workspace boundary comprises a first three dimensional shape and the second virtual workspace boundary comprises a second three dimensional shape that encompasses the first three dimensional shape. In some aspects, an area between the first three dimensional shape and the second three dimensional shape defines a warning zone that indicates the user input device is nearing the second workspace limit. In still further aspects, the first virtual workspace boundary comprises a cube. The portion of the first virtual workspace boundary operable to move may be a side wall of the cube. In some aspects, determining the location may include detecting that the portion of the first virtual workspace boundary has moved closer to the second virtual workspace boundary, and the method may further include in response to the detecting, providing user feedback. The feedback may include changing a visual characteristic of the first virtual workspace boundary. Determining the location may include detecting that the portion of the first virtual workspace boundary intersects with the second virtual workspace boundary, and the method further includes in response to the detecting, providing user feedback. The feedback may include changing a visual characteristic of the first virtual workspace boundary or the second virtual workspace boundary. The feedback may include an audible alert or haptic feedback. The user input device may be an ungrounded user input device.

In another aspect, a method of determining a location of an ungrounded user input device of a surgical robotic system within a surgical workspace includes determining, by one or more processors communicatively coupled to the surgical robotic system, whether a user is engaging with an ungrounded user input device; in response to determining the user is engaging with the ungrounded user input device, determining, by one or more processors communicatively coupled to the surgical robotic system, whether the ungrounded user input device is within a warning zone of the surgical workspace; and in response to determining the user input device is within the warning zone, providing user feedback corresponding to a location of the user input device relative to the surgical workspace. The surgical workspace may include a workspace limit beyond which the ungrounded user input device is inoperable to control a surgical robotic instrument, and the warning zone comprises an area of the surgical workspace near the workspace limit. In some aspects, determining the ungrounded user input device is within a warning zone comprises: providing a first virtual three-dimensional boundary representing an inner boundary of the warning zone; providing a second virtual three-dimensional boundary representing a workspace limit beyond which the ungrounded user input device is inoperable to control a surgical robotic instrument, the second virtual three-dimensional boundary encompasses the first virtual three-dimensional boundary; and determining a location of the user input device within the surgical workspace corresponds to an area between the first virtual three-dimensional boundary and the second virtual three-dimensional boundary. In some aspects, providing user feedback comprises providing the user with information indicating the user input device is near a workspace limit of the surgical workspace. In other aspects, providing user feedback comprises providing the user with information indicating the user input device has exceeded a workspace limit of the surgical workspace. The surgical workspace may include a workspace limit defined by a plurality of sides, and providing user feedback comprises providing the user with information indicating which of the plurality of sides the user input device is closest to. The plurality of sides may define a workspace limit having a three-dimensional shape. The user input device may be a first user input device, and the surgical robotic system may further include a second user input device, and providing user feedback comprises providing the user with information indicating whether the first user input device or the second user input device is in the warning zone. The surgical workspace may include a three-dimensional shape and providing user feedback further comprises providing the user with information indicating which side of the three-dimensional shape the first user input device or the second user input device is closest to. The feedback may include a visual feedback on a display of the surgical robotic system. The visual feedback may include at least one icon, and a location of the at least one icon on the display indicates the location of the user input device relative to the surgical workspace. The visual feedback may include at least one icon, and a location of the at least one icon on the display indicates whether the user input device within the warning zone is a left user input device or a right user input device. The visual feedback may include at least one icon, and a size or shape of the at least one icon changes to indicate the location of the user input device relative to the surgical workspace.

In another aspect, a method of determining a position of a user input device of a surgical robotic system within a surgical workspace based on a virtual workspace, the method comprising: determining, by one or more processors communicatively coupled to the surgical robotic system, whether a user controlling the user input device is in at least one mode of operation selected from a training mode, a pre-usage reminder mode, and a feedback during usage mode; in response to determining the user is in a training mode, assigning a user input device training operation to be performed within a virtual workspace boundary corresponding to the surgical workspace; in response to determining the user is in a pre-usage reminder mode, assigning a user input device engagement operation to be performed within the virtual workspace boundary after at least one other engagement operation is performed; and in response to determining the user is in a feedback during usage mode, determining whether the user input device is within a warning zone of the surgical workspace, and upon determining the user input device is within the warning zone, providing user feedback. The training mode may occur prior to a teleoperation mode in which the user input device is operable to control a surgical robotic instrument, and the training operation comprises moving the user input device without exceeding the virtual workspace boundary. The pre-usage reminder mode may occur prior to a teleoperation mode in which the user input device is operable to control a surgical robotic instrument, and the at least one other engagement operation comprises positioning a chair of the surgical robotic system to a position suitable for teleoperation, and the engagement operation comprises moving the user input device to a side of the virtual workspace boundary. The feedback during usage mode may occur during a teleoperation mode in which the user input device is operable to control a surgical robotic instrument, and providing feedback comprises indicating to the user (1) the user input device is nearing a side of the surgical workspace, (2) which side of the surgical workspace the user input device is closest to or (3) whether the user input device is a left user input device or a right user input device.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment of the invention in this disclosure are not necessarily to the same embodiment, and they mean at least one. Also, in the interest of conciseness and reducing the total number of figures, a given figure may be used to illustrate the features of more than one embodiment of the invention, and not all elements in the figure may be required for a given embodiment.

FIGS. 17A-17J provide examples of the visual feedback that may be provided to the user during the Feedback During Usage mode.

DETAILED DESCRIPTION

Figure 1:
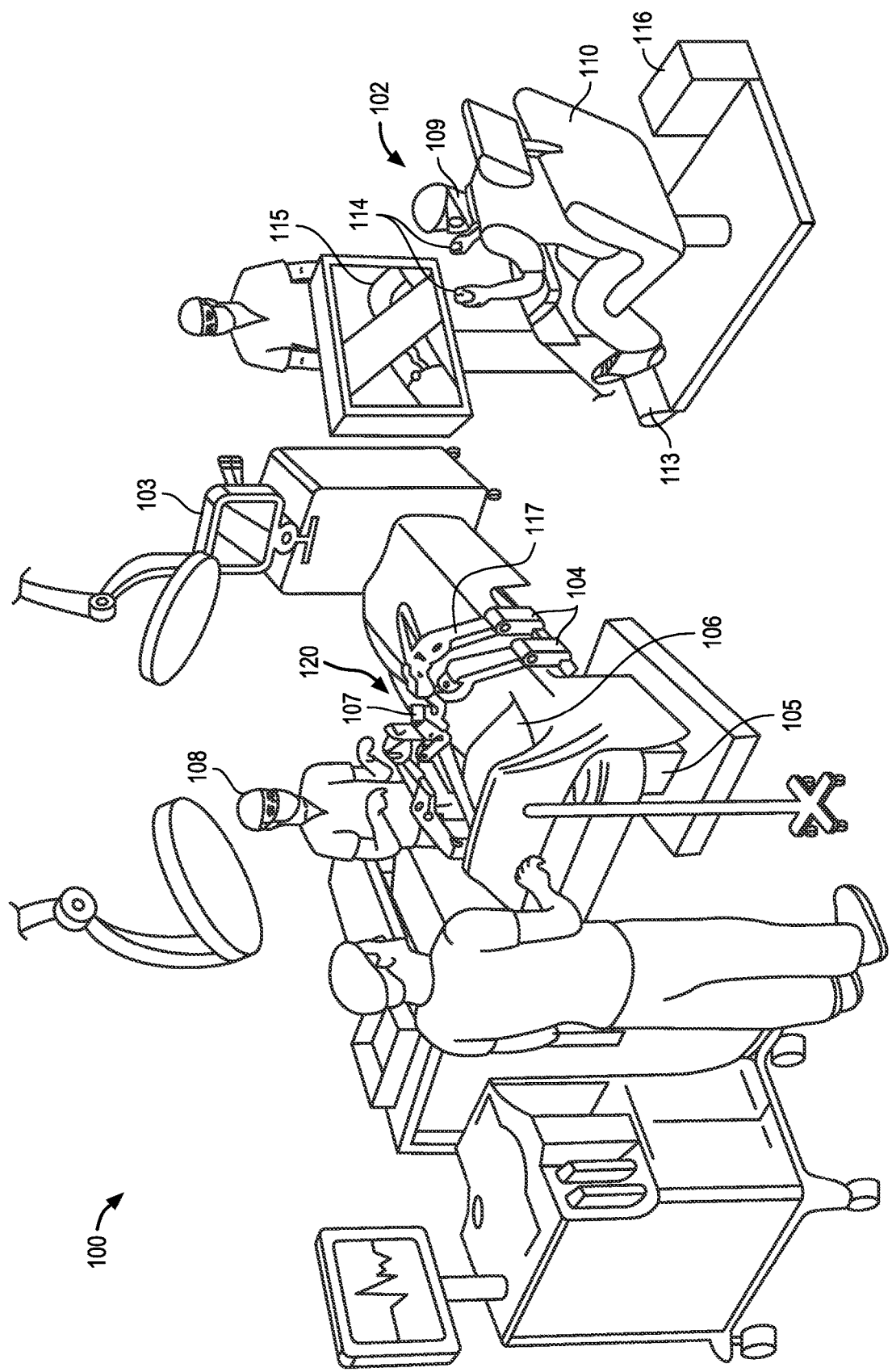
FIG. 1 is a pictorial view of an example surgical robotic system in an operating arena, in accordance with an embodiment.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

In addition, the terminology used herein is for the purpose of describing particular aspects only and is not intended to be limiting of the invention. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a", "an", and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

The terms "or" and "and/or" as used herein are to be interpreted as inclusive or meaning any one or any combination. Therefore, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

Moreover, the use of relative terms throughout the description may denote a relative position or direction. For example, "distal" may indicate a first direction away from a reference point, e.g., away from a user. Similarly, "proximal" may indicate a location in a second direction opposite to the first direction, e.g., toward the user. Such terms are provided to establish relative frames of reference, however, and are not intended to limit the use or orientation of any particular surgical robotic component to a specific configuration described in the various embodiments below.

Referring to FIG. 1, this is a pictorial view of an example surgical robotic system 100 in an operating arena. The surgical robotic system 100 includes a user console 102, a control tower 103, and one or more surgical robots 120, including robotic arms 104 at a surgical robotic platform 105, e.g., an operating table, a bed, etc. The system 100 can incorporate any number of devices, tools, or accessories used to perform surgery on a patient 106. For example, the system 100 may include one or more surgical tools 107 used to perform surgery. A surgical tool 107 may be an end effector that is attached to a distal end of a surgical arm 104, for executing a surgical procedure.

Each surgical tool 107 may be manipulated manually, robotically, or both, during the surgery. For example, the surgical tool 107 may be a tool used to enter, view, or manipulate an internal anatomy of the patient 106. In an embodiment, the surgical tool 107 is a grasper that can grasp tissue of the patient. The surgical tool 107 may be controlled manually, by a bedside operator 108; or it may be controlled robotically, via actuated movement of the surgical robotic arm 104 to which it is attached. The surgical robotic arms 104 are shown as a table-mounted system, but in other configurations the surgical robotic arms 104 may be mounted in a cart, ceiling or sidewall, or in another suitable structural support.

Generally, a remote operator 109, such as a surgeon or other operator, may use the user console 102 to remotely manipulate the surgical robotic arms 104 and/or the attached surgical tools 107, e.g., teleoperation. The user console 102 may be located in the same operating room as the rest of the system 100, as shown in FIG. 1. In other environments however, the user console 102 may be located in an adjacent or nearby room, or it may be at a remote location, e.g., in a different building, city, or country. The user console 102 may comprise a seat 110, one or more user interface devices, for example, foot-operated controls 113 or handheld user input devices (UID) 114, and at least one user display 115 that is configured to display, for example, a view of the surgical site inside the patient 106. In the example user console 102, the remote operator 109 is sitting in the seat 110 and viewing the user display 115 while manipulating a foot-operated control 113 and a handheld UID 114 in order to remotely control the arms 104 and the surgical tools 107 (that are mounted on the distal ends of the arms 104).

In some variations, the bedside operator 108 may also operate the system 100 in an "over the bed" mode, in which the bedside operator 108 (user) is now at a side of the patient 106 and is simultaneously manipulating a robotically-driven tool (end effector as attached to the arm 104), e.g., with a handheld UID 114 held in one hand, and a manual laparoscopic tool. For example, the bedside operator's left hand may be manipulating the handheld UID 114 to control a robotic component, while the bedside operator's right hand may be manipulating a manual laparoscopic tool. Thus, in these variations, the bedside operator 108 may perform both robotic-assisted minimally invasive surgery and manual laparoscopic surgery on the patient 106.

During an example procedure (surgery), the patient 106 is prepped and draped in a sterile fashion to achieve anesthesia. Initial access to the surgical site may be performed manually while the arms of the robotic system 100 are in a stowed configuration or withdrawn configuration (to facilitate access to the surgical site). Once access is completed, initial positioning or preparation of the robotic system 100 including its arms 104 may be performed. Next, the surgery proceeds with the remote operator 109 at the user console 102 utilizing the foot-operated controls 113 and the UIDs 114 to manipulate the various end effectors and perhaps an imaging system, to perform the surgery. Manual assistance may also be provided at the procedure bed or table, by sterile-gowned bedside personnel, e.g., the bedside operator 108 who may perform tasks such as retracting tissues, performing manual repositioning, and tool exchange upon one or more of the robotic arms 104. Non-sterile personnel may also be present to assist the remote operator 109 at the user console 102. When the procedure or surgery is completed, the system 100 and the user console 102 may be configured or set in a state to facilitate post-operative procedures such as cleaning or sterilization and healthcare record entry or printout via the user console 102.

In one embodiment, the remote operator 109 holds and moves the UID 114 to provide an input command to move a robot arm actuator 117 in the robotic system 100. The UID 114 may be communicatively coupled to the rest of the robotic system 100, e.g., via a console computer system 116. Representatively, in some embodiments, UID 114 may be a portable handheld user input device or controller that is ungrounded with respect to another component of the surgical robotic system. For example, UID 114 may be ungrounded while either tethered or untethered from the user console. The term "ungrounded" is intended to refer to implementations where, for example, both UIDs are neither mechanically nor kinematically constrained with respect to the user console. For example, a user may hold a UID 114 in a hand and move freely to any possible position and orientation within a workspace, only limited by, for example, a predetermined three-dimensional surgical workspace limit or boundary recognized by the system 100. Representatively, the system may include a tracking mechanism that tracks the location of the UID 114 within, and relative to, the surgical workspace limit or boundary. The UID 114 can generate spatial state signals corresponding to movement of the UID 114, e.g., position and orientation of the handheld housing of the UID, and the spatial state signals may be input signals to control a motion of the robot arm actuator 117. The signals (e.g., tracking sensor signals, clutch signals or engage/disengage teleoperation mode signals) may be wirelessly communicated between UID 114 and the computer system 116. In addition, a power source, such as a rechargeable battery, may be stored within the housing of UID 114 so that it does not need to be mechanically connected to a power source, such as by a wire or cable. The robotic system 100 may use control signals derived from the spatial state signals, to control proportional motion of the actuator 117. In one embodiment, a console processor of the console computer system 116 receives the spatial state signals and generates the corresponding control signals. Based on these control signals, which control how the actuator 117 is energized to move a segment or link of the arm 104, the movement of a corresponding surgical tool that is attached to the arm may mimic the movement of the UID 114. Similarly, interaction between the remote operator 109 and the UID 114 can generate for example a grip control signal that causes a jaw of a grasper of the surgical tool 107 to close and grip the tissue of patient 106.

The surgical robotic system 100 may include several UIDs 114, where respective control signals are generated for each UID that control the actuators and the surgical tool (end effector) of a respective arm 104. For example, the remote operator 109 may move a first UID 114 (e.g., a left UID) to control the motion of an actuator 117 that is in a left robotic arm, where the actuator responds by moving linkages, gears, etc., in that arm 104. Similarly, movement of a second UID 114 (e.g., a right UID) by the remote operator 109 controls the motion of another actuator 117, which in turn moves other linkages, gears, etc., of the robotic system 100. The robotic system 100 may include a right arm 104 that is secured to the bed or table to the right side of the patient, and a left arm 104 that is at the left side of the patient. An actuator 117 may include one or more motors that are controlled so that they drive the rotation of a joint of the arm 104, to for example change, relative to the patient, an orientation of an endoscope or a grasper of the surgical tool 107 that is attached to that arm. Motion of several actuators 117 in the same arm 104 can be controlled by the spatial state signals generated from a particular UID 114. The UIDs 114 can also control motion of respective surgical tool graspers. For example, each UID 114 can generate a respective grip signal to control motion of an actuator, e.g., a linear actuator, that opens or closes jaws of the grasper at a distal end of surgical tool 107 to grip tissue within patient 106.

In some aspects, the communication between the platform 105 and the user console 102 may be through a control tower 103, which may translate user commands that are received from the user console 102 (and more particularly from the console computer system 116) into robotic control commands that are transmitted to the arms 104 on the robotic platform 105. The control tower 103 may also transmit status and feedback from the platform 105 back to the user console 102. The communication connections between the robotic platform 105, the user console 102, and the control tower 103 may be via wired and/or wireless links, using any suitable ones of a variety of data communication protocols. Any wired connections may be optionally built into the floor and/or walls or ceiling of the operating room. The robotic system 100 may provide video output to one or more displays, including displays within the operating room as well as remote displays that are accessible via the Internet or other networks. The video output or feed may also be encrypted to ensure privacy and all or portions of the video output may be saved to a server or electronic healthcare record system. It will be appreciated that the operating room scene in FIG. 1 is illustrative and may not accurately represent certain medical practices.

As previously discussed, a UID 114 of the surgical robotic system 100 may be used to control the actuators and the surgical tool (end effector) of a respective arm 104 once certain operational conditions are met. Representatively, to control the actuators and/or surgical tool, the user may hold the UID 114 and perform at least one intentional action that indicates the user is ready to control the actuators and/or surgical tool in a teleoperation mode. The teleoperation mode is a mode of the surgical robotic system in which the user is actively controlling, or is able to actively control, the surgical robotic system components, e.g., an actuator, a robotic arm, a surgical tool and/or endoscope, for example, with a user input device or foot pedal. For example, the intentional action may be a gesture detected by the user input device, such as the user tapping on the user input device or squeezing the user input device. Alternatively, the action may be an action which results in the user input device being in a particular location, orientation and/or position, such as the user docking the user input device in a docking station or positioning the user input device in close proximity to the docking station. On the other hand, when the user is unable to actively control the surgical robotic system components, the system is considered to have exited the teleoperation mode, be out of the teleoperation mode, be in a non-teleoperation mode or have disengaged the teleoperation mode. For example, the system may be considered to have exited or disengaged the teleoperation mode or be in a non-teleoperation mode when (1) no user input is accepted by the surgical robotic system, (2) user input commands to a graphical user interface (GUI) of the system are accepted, but cannot control the associated surgical robotic system components or (3) the user is not yet able to control the surgical robotic components, but a sequence of intentional actions would cause the user to enter or engage teleoperation mode. Once in teleoperation mode, movement of the UID 114 by the user within a defined workspace area controls the actuators and/or surgical tool.

As previously discussed, when the UID 114 is an ungrounded (e.g., mid-air) controller, the workspace within which the UID 114 is able to control components of the system is an invisible surgical workspace the user needs to learn before she or he can use the UID 114 during teleoperation. Therefore, in one aspect, the system may implement a multimodal process to help the user learn, understand and work within the invisible workspace. For example, the multimodal process may include three modes or categories: (1) Training, (2) Pre-Usage Reminder and (3) Feedback During Usage. The Training mode may occur prior to any surgical operations (e.g., prior to the teleoperation mode) and allow the user to build a mental model of where they are allowed to move the UID. The Pre-Usage Reminder mode may also occur prior to a surgical operation (e.g., immediately before the user engages in teleoperation mode) and may remind the user of the workspace boundary or limits prior to using the UID 114. The Feedback During Usage mode may occur during the teleoperation mode, for example, when the user is using the UID 114 to operate a surgical component, and give real-time feedback about the location of the UID within the workspace. The desired mode (e.g., Training, Pre-Usage Reminder and/or Feedback During Usage) may be selected by the user, or may be automatically selected by the surgical robotic system 100.

Figure 2:
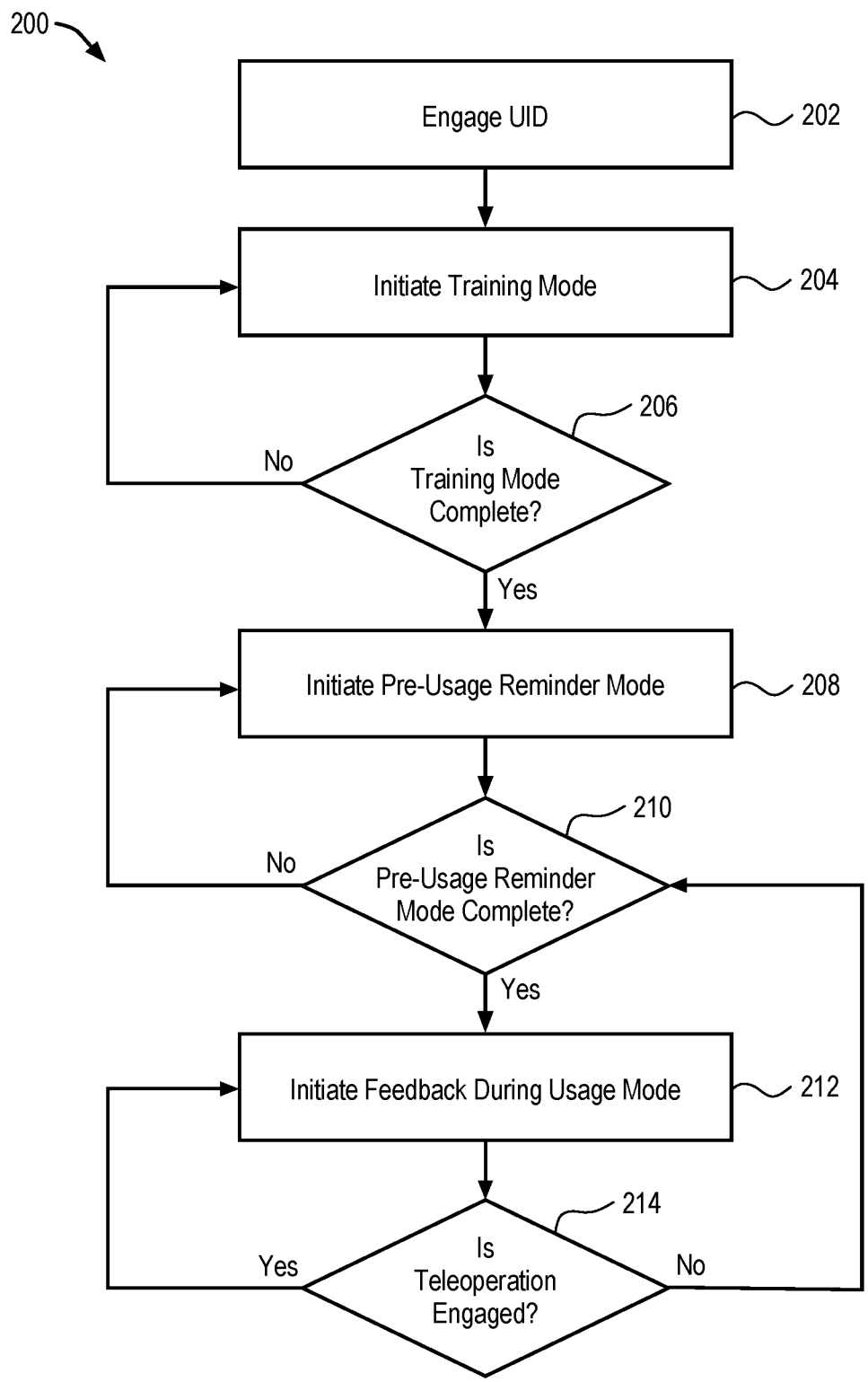
FIG. 2 provides a block diagram of an exemplary multi-modal process of a surgical robotic system.

FIG. 2 provides a block diagram of an exemplary multimodal process of a surgical robotic system. Representatively, the multi-modal process 200 may include detecting that the UID is engaged at operation 202. The engagement operation 202 may be any operation by the user that the surgical robotic system detects as the user engaging with, or otherwise holding, a UID (e.g., UID 114). For example, engagement of the UID may be detected by a sensor (e.g., a proximity or pressure sensor coupled to the UID) that detects when a user holds or grasps UID 114 with a hand, performs a gesture with the UID, or some other predefined active operation by the user that the system recognizes as meaning the user is engaging with the UID 114. Once engagement is detected, a Training mode may be initiated at operation 204. The Training mode may be automatically initiated by the system once engagement of a UID is detected, or selected manually by a user. As previously discussed, the Training mode occurs prior to any surgical operations (e.g., prior to the teleoperation mode) and allows the user to build a mental model of where they are allowed to move the UID. The Training mode will be discussed in more detail in reference to FIGS. 3, 4A-B and 5A-B.

The system then determines whether the Training mode has been completed by the user at operation 206. If the Training mode is not completed, the Training mode may continue, restart, repeat, etc., depending on where the user is at in the training operation. Once the Training mode is completed, the Pre-Usage Reminder mode is initiated at operation 208. As previously discussed, the Pre-Usage Reminder mode may also occur prior to a surgical operation, for example immediately before the user engages in teleoperation mode, and may remind the user prior to using the UID 114 of the workspace. The Pre-Usage Reminder mode will be discussed in more detail in reference to FIG. 6.

The system then determines whether the Pre-Usage Reminder mode is completed by the user at operation 210. If the Pre-Usage Reminder mode is not completed by the user, the system returns to operation 208 until the Pre-Usage Reminder mode is completed. Once the Pre-Usage Reminder mode is completed, the Feedback During Usage mode is initiated at operation 212. The Feedback During Usage mode may occur during the teleoperation mode, for example, when the user is using the UID 114 to operate a surgical component, and give real-time feedback about the location of the UID within the workspace. The Feedback During Usage mode will be discussed in more detail in reference to FIGS. 7-18H.

The system then determines at operation 214 whether a teleoperation mode is also engaged. If it is, the process returns to operation 212 and the Feedback During Usage mode continues until the system determines teleoperation is no longer engaged. If teleoperation is no longer engaged, for example because the UID is no longer within the workspace limit, the process may return to the Pre-Usage Reminder mode at operation 210. The user will then continue in the Pre-Usage Reminder mode until the system determines it can proceed to the Feedback During Usage mode (e.g., the Reminder mode is completed and teleoperation is engaged). It should be understood that although the Training, Pre-Usage Reminder and Feedback During Usage modes are described one after the other in FIG. 2, it should be understood that other modes (e.g., disengagement of teleoperation, etc.) may occur between each of these modes and they do not necessarily have to occur during any particular time frame. For example, the Training mode 204 could occur over a series of days, and once completed, need not occur again before the Pre-Usage Reminder mode 208.

Figure 3:
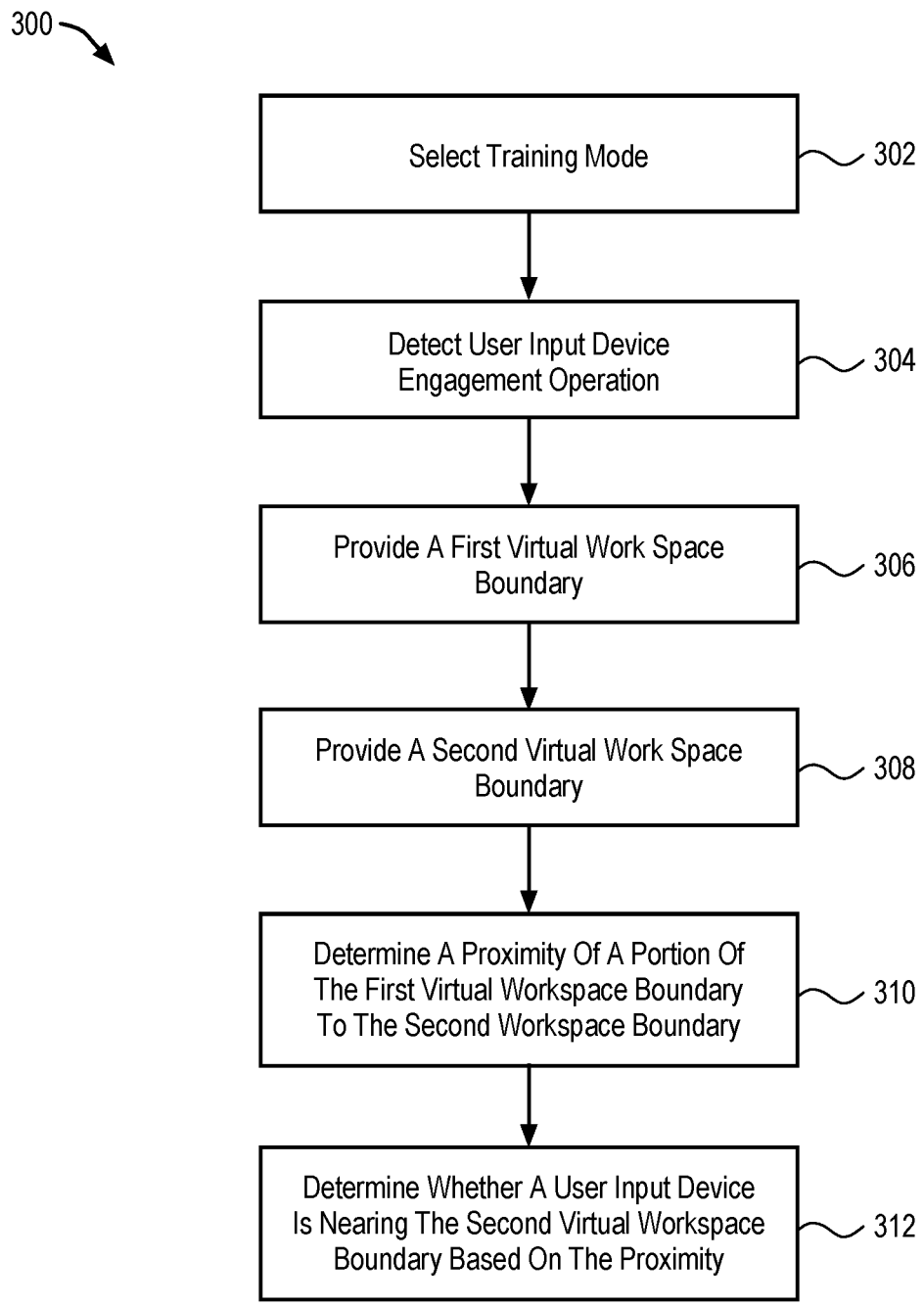
FIG. 3 provides a block diagram of an exemplary Training mode of a surgical robotic system.

Referring now to the various modes in more detail, FIG. 3 provides a block diagram of an exemplary Training mode of a surgical robotic system. The Training mode 300 (e.g., operation 204 of FIG. 2) may include a task that is specifically designed to help the user learn the boundary of the workspace area. The user may be instructed or guided so they can fully focus on the designated task so that they can create a mental model of the workspace. Representatively, Training mode 300 may begin when the training mode is selected at operation 302 (e.g., by the user) and a user input device engagement operation 302 is detected by the surgical robotic system 304. The engagement operation 302 may be any operation by the user that the surgical robotic system detects as the user engaging with, or otherwise holding, a UID (e.g., UID 114). For example, engagement of the UID may be detected by a sensor (e.g., a proximity or pressure sensor coupled to the UID) that detects when a user holds or grasps UID 114 with a hand, performs a gesture with the UID, or some other predefined active operation by the user that the system recognizes as meaning the user is engaging with the UID 114. Once engagement is detected, a first virtual workspace boundary may be provided at operation 306. The first virtual workspace boundary may be displayed to the user and provide a visual representation of the real surgical workspace within which the UID should be manipulated in order to operate an associated surgical component (e.g., a surgical tool). In other words, as long as the operator is manipulating the UID within a real workspace area that corresponds to the virtual area defined by the first virtual workspace boundary, the user will be able to control an associated surgical component during a real surgical procedure. The movement of the real UID may be tracked by a tracking device of the surgical robotic system and the movement may be displayed as a corresponding virtual movement of a virtual UID relative to the first virtual workspace boundary. The user can therefore see whether they are within the workspace boundary or limit, or exceeding the boundary or limit, and begin to understand the workspace limits they should stay within during a real procedure. As previously mentioned, the first virtual workspace boundary may represent a desired area within which the UID should be during a surgical procedure. If the virtual UID exceeds the first virtual workspace boundary, the real UID may still be able to control an associated surgical component, but be considered within a "warning zone." The "warning zone" may be an area of operation or workspace region that is considered too close to a boundary or limit where the UID is no longer allowed to control an associated component. In this aspect, the first virtual workspace boundary may also be referred to as a boundary for the warning zone.

To indicate to the user the workspace limit, boundary or region beyond which control of an associated surgical component by the UID is no longer allowed (e.g., the UID is too far outside of the workspace), the training operation also provides the user with a second virtual workspace boundary at operation 308. The second virtual workspace boundary may be displayed to the user and provide a visual representation of an area within which the UID must be manipulated in order to operate an associated surgical component (e.g., a surgical tool). If the movement of the UID exceeds the second virtual workspace boundary, the UID is considered to have exceeded the workspace limit or boundary and is prevented from controlling an associated surgical component by the system. In some cases, the teleoperation mode is disengaged in response to detecting that the workspace boundary or limit has been met or exceeded by the UID. In this aspect, the second virtual workspace boundary may be displayed to the user as a boundary or limit that is outside of the first virtual workspace boundary. For example, in some aspects, the first virtual workspace boundary and the second virtual workspace boundary may be displayed to the user as three-dimensional shapes. The three-dimensional shape of the second virtual workspace boundary may be larger (e.g., define a larger area) than that of the first virtual workspace boundary. In this aspect, the three-dimensional shapes may be displayed to the user as one inside of the other. For example, the three-dimensional shape of the first virtual workspace boundary may displayed to the user as located within, or otherwise encompassed by, the three-dimensional shape of the second virtual workspace boundary. In this aspect, the area within (or at) the boundary of the inner three-dimensional shape (e.g., the first virtual workspace) may be understood by the user as the desired area of operation of the UID. The area or zone between the inner three-dimensional boundary (e.g., the first virtual workspace boundary) and the outer three-dimensional boundary (e.g., the second virtual workspace boundary) may be understood by the user as the warning zone or area indicating the user is approaching the operation limit of the UID. The area beyond (or at) the outer three-dimensional boundary (e.g., the second virtual workspace boundary) may be understood by the user as an area in which the UID has exceeded its operational limit and is therefore no longer able to control an associated surgical component. Accordingly, when the user moves the real UID, and this movement is shown as the virtual UID exceeding the inner three-dimensional boundary, approaching the outer three-dimensional boundary, or exceeding the outer three-dimensional boundary, the user begins to recognize and learn the operational boundaries of the real workspace.

In some aspects, a portion of the inner three-dimensional boundary follows, or otherwise moves in response to, the movement of the virtual UID. Accordingly, in such cases, a proximity of the first workspace boundary (e.g., three-dimensional shape) to the second workspace boundary (e.g., three dimensional shape) may be determined (e.g., measured) at operation 310. The proximity information determined at operation 310 may then be used to determine whether the UID is nearing the second workspace boundary at operation 312.

Figure 4A:
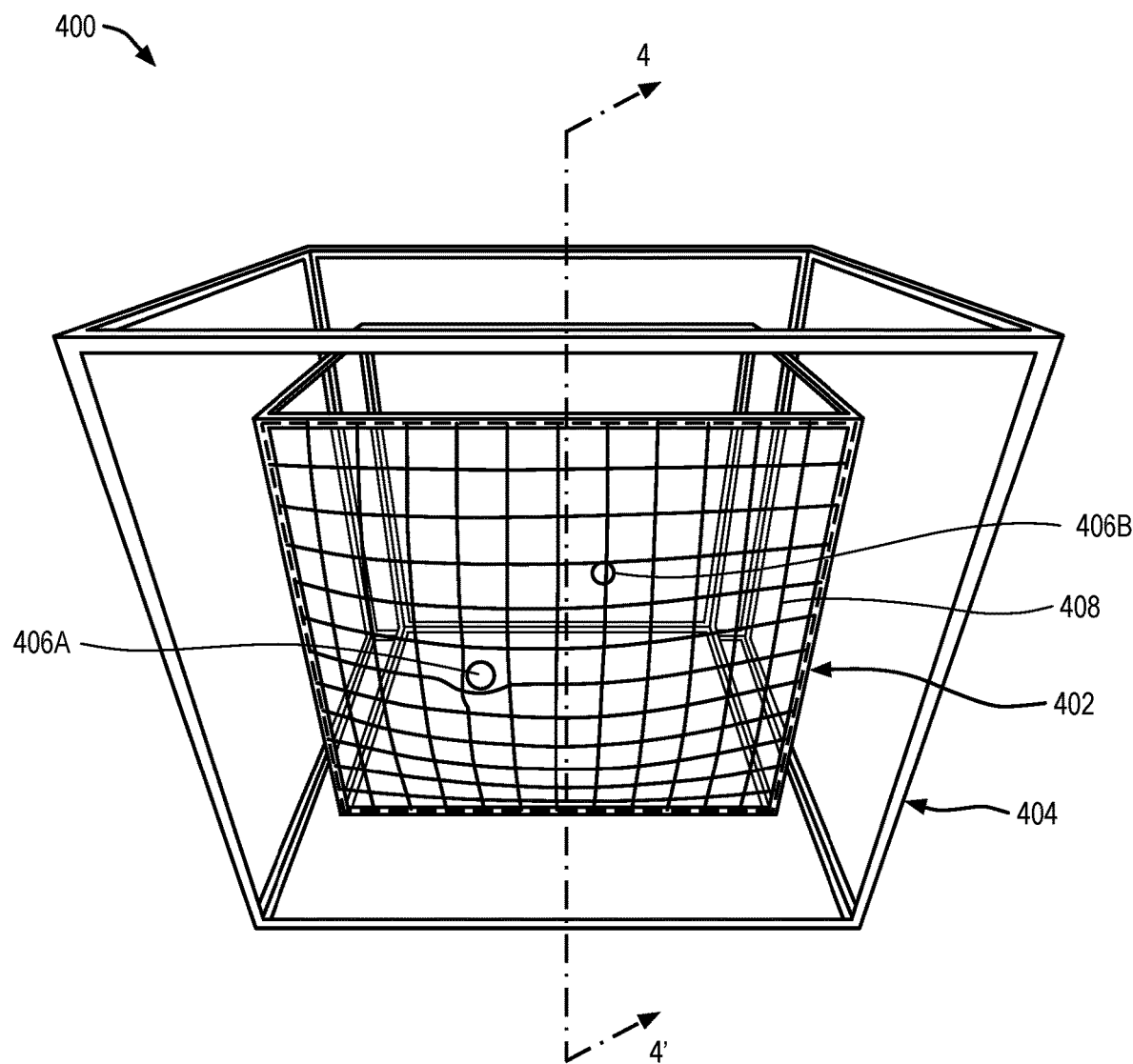
FIG. 4A schematically illustrate a representative Training operation in accordance with FIG. 3.
Figure 4B:
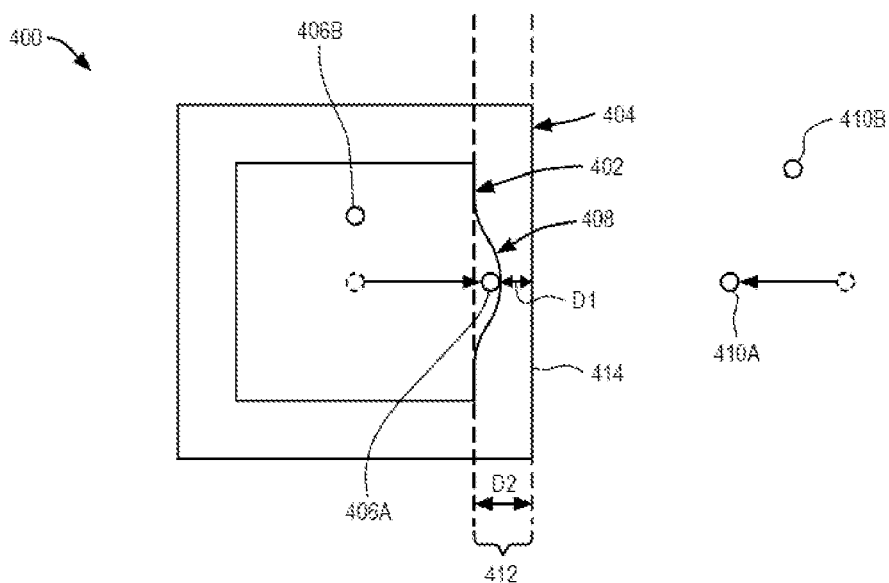
FIG. 4B illustrate cross-sectional side view of FIG. 4A along lines 4-4'.
Figure 5A:
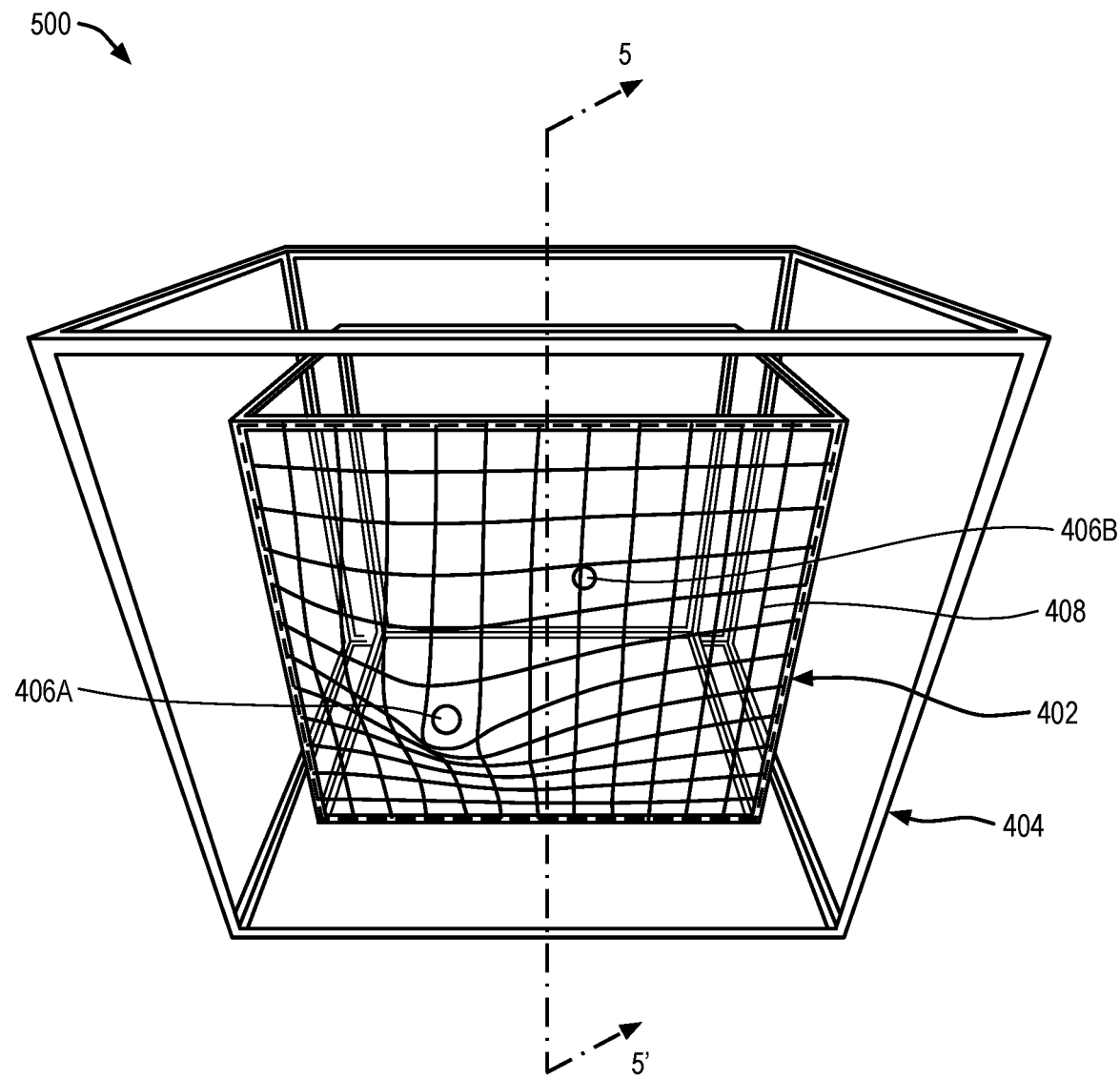
FIG. 5A schematically illustrates a representative Training operation in accordance with FIG. 3.
Figure 5B:
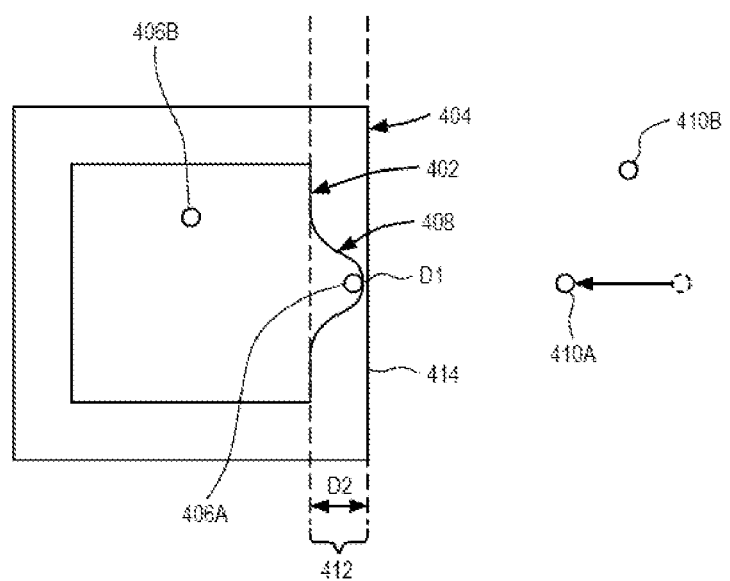
FIG. 5B illustrate cross-sectional side view of FIG. 5A along lines 5-5'.

FIG. 4A, FIG. 4B, FIG. 5A and FIG. 5C schematically illustrate representative Training operations in accordance with FIG. 3. Representatively, FIG. 4A and FIG. 5A schematically illustrate exemplary three-dimensional shapes corresponding to the virtual workspace boundaries, and which are displayed to the user, as described in training operation 200. FIG. 4B and FIG. 5B illustrate cross-sectional side views of FIG. 4A and FIG. 5A along lines 4-4' and 5-5', respectively.

Referring now in more detail to FIG. 4A, FIG. 4A illustrates a training operation 400 in which a first virtual workspace boundary 402 and a second virtual workspace boundary 404 are displayed to the user as three-dimensional cube or box-shaped workspaces. For example, the first virtual workspace boundary 402 may be an inner three-dimensional cube or box-shaped workspace and the second virtual workspace boundary 404 may be an outer three-dimensional cube or box-shaped workspace encompassing the inner cube or box-shaped workspace. The three-dimensional shapes may be a virtual workspace or area within the bounds of which the user can learn to operate the UID. The virtual workspace, in turn, represents the area of the real workspace boundary or limit within which the surgeon can use the real UID. The inner three-dimensional shape (e.g., boundary 402) may represent an inner boundary of a warning zone within the actual workspace (e.g., an area considered close to or near an actual workspace limit). The outer three-dimensional shape (e.g., boundary 404) may represent the boundary of the real workspace limit (e.g., the boundary beyond which the UID is no longer operable).

Although not shown, each of the three-dimensional cube or box-shaped workspaces may be considered bounded by six square faces, facets or sides, that are connected by lines as shown. For example, in operation 400, virtual UIDs 406A-B are displayed to the user as located within boundary 402 and/or boundary 404. At least one face or side 408 of the three-dimensional shape forming the first workspace boundary 402 is also displayed to the user. The side 408 may be flexible such that it moves outward when a UID exceeds boundary 402. For example, as shown in operation 400, UID 406A exceeds the boundary 402, while UID 406B is within boundary 402. This outward movement of the side 408 in response to the movement of the UID 406A signals to the user that the movement of the UID 406A has exceeded boundary 402. In other words, the UID 406A is now in the warning zone between boundary 402 and boundary 404. Since the movement of UID 406A is mapped to the movement of the real UID 310A within the real workspace, the user begins to learn the workspace boundaries and when they are nearing a workspace limit. In some aspects, the proximity of the boundary 402 to boundary 404 can therefore be used to determine the UID locations within the workspaces, and whether the UIDs are nearing the boundaries 402, 404.

Representatively, FIG. 4B shows a cross-sectional side view of FIG. 4A, along line 4-4'. From this view, it can be seen that the movement of the real UID 410A is causing virtual UID 406A to exceed boundary 402, while the movement of UID 410B is within the boundary 402, therefore UID 406B is shown within boundary 402. The movement of UID 406A pushes side 408 of boundary 402 outward toward boundary 404. In other words, UID 406A is now within the warning zone 412 between boundary 402 and boundary 404.

Since UID 406A moves side 408 when it reaches or exceeds the boundary 402, the proximity of the side 408 relative to the side 414 of boundary 404 can be used to determine if the UID is nearing a workspace boundary or limit, and a location of the UID within the workspace in general. For example, when it is determined that a distance D1 between side 408 and side 414 near UID 406A is less than a predetermined distance D2 (e.g., distance between sides 408 and 314 when not pushed out by the UID), the system indicates to the user that the UID is nearing the boundary 404 (e.g., within the warning zone).

In some aspects, additional alerts may be provided to inform the user that they are nearing or exceeding a workspace boundary. For example, in some aspects, a visual characteristic of one or more of boundaries 402, 404 and/or UIDs 406A-B may change to alert the user that they are nearing or exceeding a workspace boundary. The visual characteristic may, for example, be a change in the color of one or more of the boundaries or UIDs when within a warning zone or workspace limit. For example, side 408 of boundary 402 may be a first color when it is in its normal position and not being pushed out by a UID. When a UID causes side 408 to move toward boundary 404 (e.g., into the warning zone), side 408 may turn a second color. Still further, when side 408 is pushed out so far that it intersects with boundary 404, it may turn a third color. For example, side 408 may be black when in the normal position, turn orange when in the warning zone and turn red when it intersects boundary 404. In addition, the outer boundary 404 may turn a different color depending on the proximity of boundary 402 to boundary 404. For example, when side 408 of boundary 402 intersects with boundary 404, boundary 404 may change from a first color to a second color (e.g., from black to red). In still further aspects, the alert may be an audible alarm or haptic response that occurs when the user is nearing or exceeding a workspace limit.

FIG. 5A-B illustrates an operation 500 in which the UID is shown exceeding the workspace limit and therefore no longer operable. Representatively, as can be seen from FIG. 5A-B, UID 406A has exceeded boundary 402 and is within (or exceeding) boundary 404. This operation can be both visually displayed to the user as shown in FIG. 5A, and determined by the system based on a proximity of the side 408 of boundary 402 relative to the side 314 of boundary 404 as shown in FIG. 5B. For example, when side 408 intersects with side 314, D1 may equal D2, and operation 400 determines that the boundary 404 has been met or exceeded. Once boundary 404 is met or exceeded, UID is no longer within a workspace in which it is allowed to operate the associated surgical component, and the system alerts the user (e.g., visual color changes, audible alarm, haptic response, etc.). This, in turn, helps the user understand the corresponding real workspace boundaries within which the real UID must be used.

In some aspects, to further assist the user in learning the workspace limits, the system may assign the user with a task that asks the user to move one or more of the UIDs around without going out of the boundary 402 and/or boundary 404. The task could be in combination with a "pause" button/pedal. While the "pause" button/pedal is held, the representation of the UIDs on the display are not translated with the movement of the real UIDs. A user could then be asked to move the on-screen UIDs to a location shown on the display screen without hitting the workspace limits. The virtual workspace boundaries (e.g., boundaries 402, 404) would then be visible only when the user moves the UID within the warning zone or outside a workspace limit.

Figure 6:
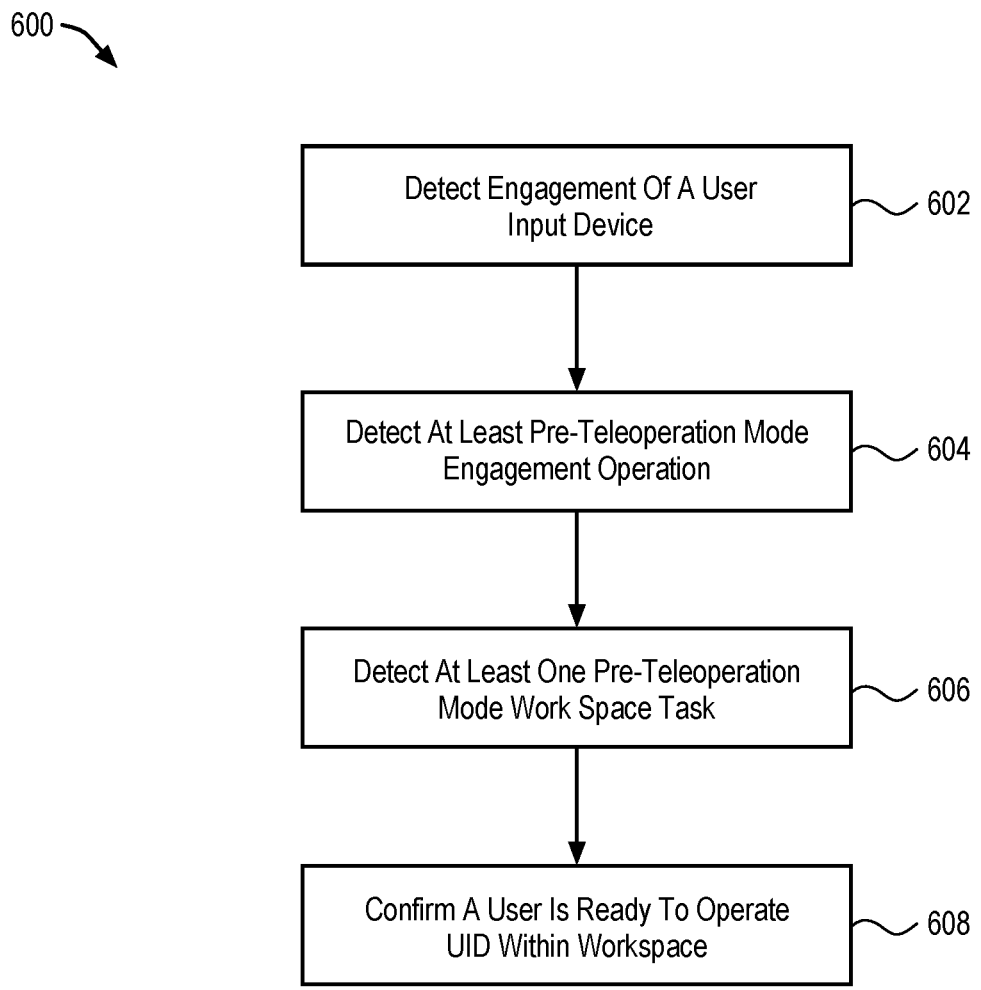
FIG. 6 provides a block diagram of an exemplary Pre-Usage Reminder mode of a surgical robotic system.

FIG. 6 provides a block diagram of an exemplary Pre-Usage Reminder mode of a surgical robotic system. As previously discussed, the Pre-Usage Reminder mode or process 600 (e.g., operation 208 of FIG. 2) may be part of an initial engagement sequence that the operator may be asked to perform to remind them of the workspace limits prior to engagement of the teleoperation mode. For example, the Pre-Usage reminder mode or process 600 may occur when the user uses the surgical robotic system for the first time that day, for the first time after a long delay, or for the first time after any predetermined period of time. Representatively, process 600 may include an initial operation of detecting an engagement of a UID at operation 602. Engagement of the UID may be detected by any of the previously discussed operations, for example, proximity or pressure sensor detecting when a user holds or grasps UID 114 with a hand, performs a gesture with the UID, or some other predefined active operation by the user that the system recognizes as meaning the user is engaging with the UID 114. Once engagement is detected, process 600 may further include detection of at least one pre-teleoperation mode engagement operation at operation 604. The at least one pre-teleoperation mode engagement operation may be, for example, the user positioning their chair to a position suitable for teleoperation, or detection of some other user or system characteristic that suggests the user is about to engage in teleoperation. Once a pre-teleoperation mode engagement operation is detected, the process includes detecting at least one pre-teleoperation mode workspace task at operation 606. The pre-teleoperation mode workspace task may be any task that reminds the user of the boundaries or limits of the workspace, and confirms to the system that the user remembers the boundaries or limits of the workspace. For example, the task could be requiring the user to hold the UID close to an edge or side of the workspace boundary or limit (e.g., close to a left edge or close to a right edge). If the user is able to move the UID within the virtual workspace close to the edge without exceeding the boundary or limit, the system determines the user remembers the boundaries or limits. If the user exceeds the edge of the boundary or limit, the system may require the user to complete one or more additional tasks until the user successfully completes the task(s). The one or more additional tasks may include, for example, moving the UID close to the same edge again, moving the UID close to another edge, or moving the UID close to multiple edges in sequence. Once the task(s) is completed successfully, the system determines that the user remembers the workspace boundaries or limits and is ready to operate the UID within the workspace at operation 608.

Figure 7:
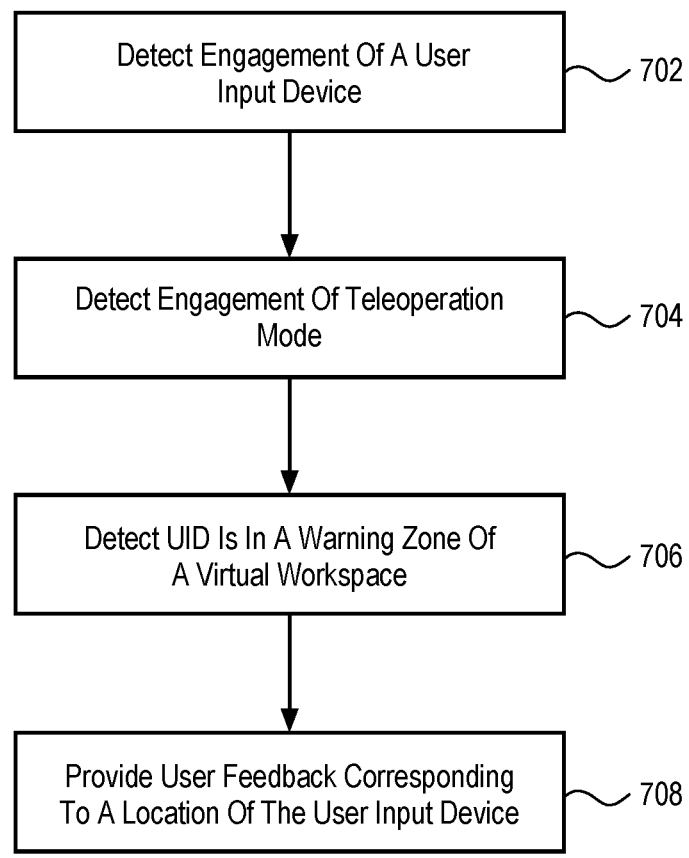
FIG. 7 provides a block diagram of an exemplary Feedback During Usage mode of a surgical robotic system.

Once both the Training mode 300 and Pre-Usage Reminder mode 600 are completed, a Feedback During Usage mode may be initiated. FIG. 7 provides a block diagram of an exemplary Feedback During Usage mode of a surgical robotic system. As previously discussed, the Feedback During Usage mode or process 700 (e.g., operation 212 of FIG. 2) may be a process which occurs while the user is operating the UID within the real workspace and provides real time feedback of the UID location relative to the workspace boundaries. Representatively, process 700 may include detecting engagement of a UID at operation 702 and detecting engagement of teleoperation mode at operation 704. Once both of these operations are detected, the system knows that the user is now manipulating the UID within the workspace and intends to use it to control a surgical component (e.g., surgical tool or instrument). The process 700 therefore continues to monitor the UID location within the workspace and can detect if the UID is in a warning zone of the virtual workspace at operation 706. If the system detects that the UID is in a warning zone, and therefore nearing the workspace limit, the system may provide feedback to the user about a location of the UID at operation 708. Representatively, the feedback may be that a UID is in the warning zone, a distance of a UID to the workspace limit when within the warning zone, whether the UID nearing the workspace limit is a left or right UID, which edge or side of the workspace limit a UID is closest to, or which tool associated with the UID location is affected. This information about the UID relative to the workspace may be determined using the proximity information previously discussed in reference to FIGS. 4A-5B. The feedback may be any one or more of the previously discussed feedback mechanisms, including a visual feedback, haptic feedback or audio feedback, or a combination of any one or more of a visual, haptic or audio feedback.

Figure 8A:
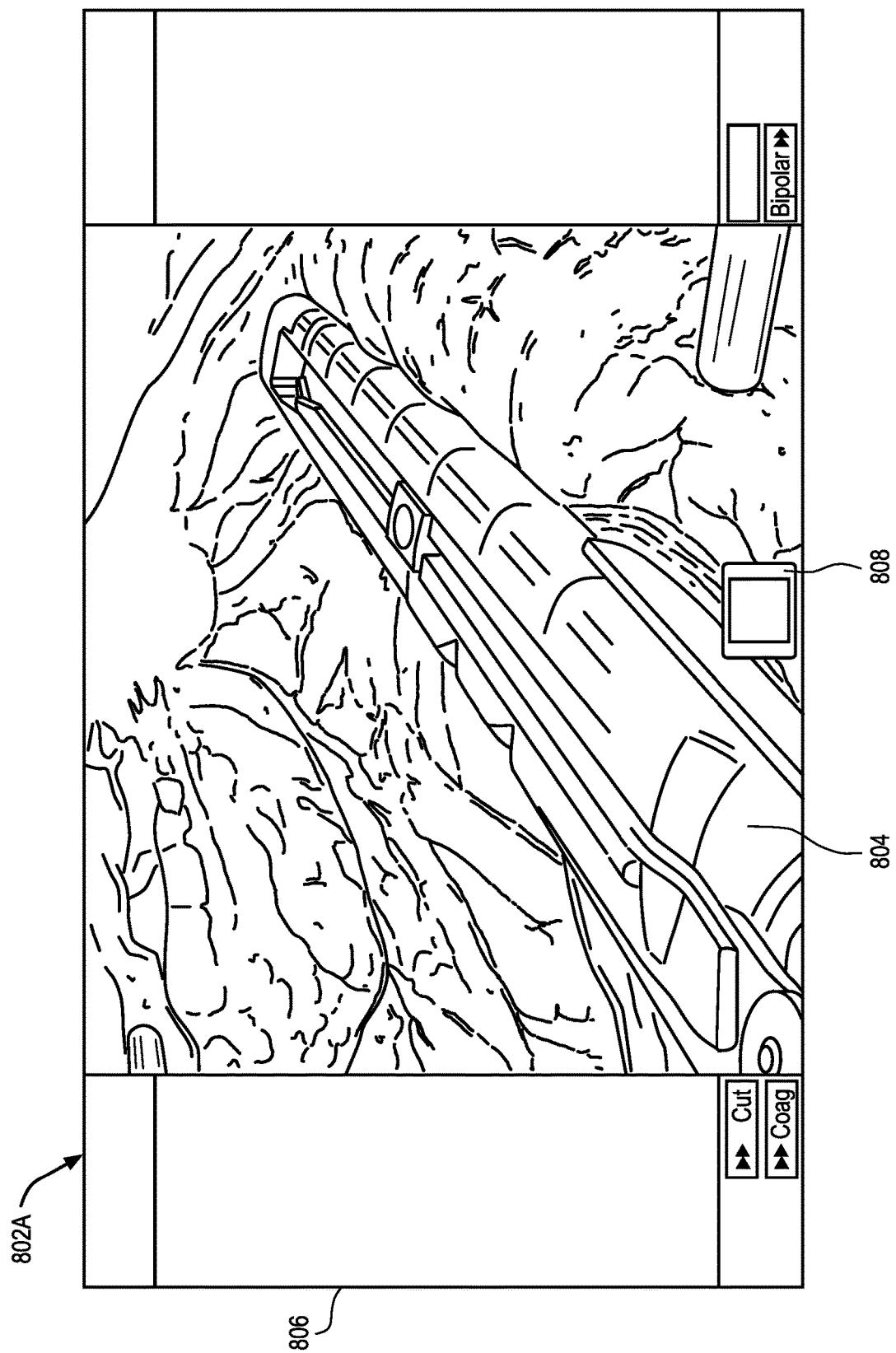
FIGS. 8A-8B provide examples of the visual feedback that may be provided to the user during the Feedback During Usage mode.

FIGS. 8A-18H provide examples of the visual feedback that may be provided to the user during the Feedback During Usage mode. Representatively, FIG. 8A illustrates a display screen 802 that the surgeon can use to view the movement of a surgical instrument 804 they are controlling with the UID during a surgical procedure on a patient 806. To provide visual feedback to the user about the UID location relative to the workspace during the surgical procedure, an indicator 808 may also appear on the display screen 802. In some aspects, the indicator 808 may only appear when the UID is determined to be in a warning zone. The indicator 808 may be a text or icon that appears in one specific location that is known to the user, but does not interfere with the user's view of the surgical procedure displayed on the screen. Since the surgeon knows where to expect the indicator 808, as soon as it appears, the user immediately recognizes that a UID is within a warning zone of the workspace and therefore nearing a workspace limit. In some aspects, the indicator 808 indicates that at least one UID is within the warning zone and close to a workspace limit, but does not indicate additional details such as which UID (e.g., left or right UID) is in the warning zone, or which boundary the UID is closest to. Since the indicator 808 does not, in this aspect, need to also indicate which UID is in the warning zone and/or a UID location relative to a boundary, the indicator may appear anywhere on the display screen 802 that can be viewed by the surgeon. For example, the indicator 808 may appear in a central area of the screen, for example, at the bottom of the screen in the center. The indicator 808 may also have any size, shape, color, or other visual characteristic that is recognized by the user as an indicator that a UID is in a warning zone.

Figure 8B:
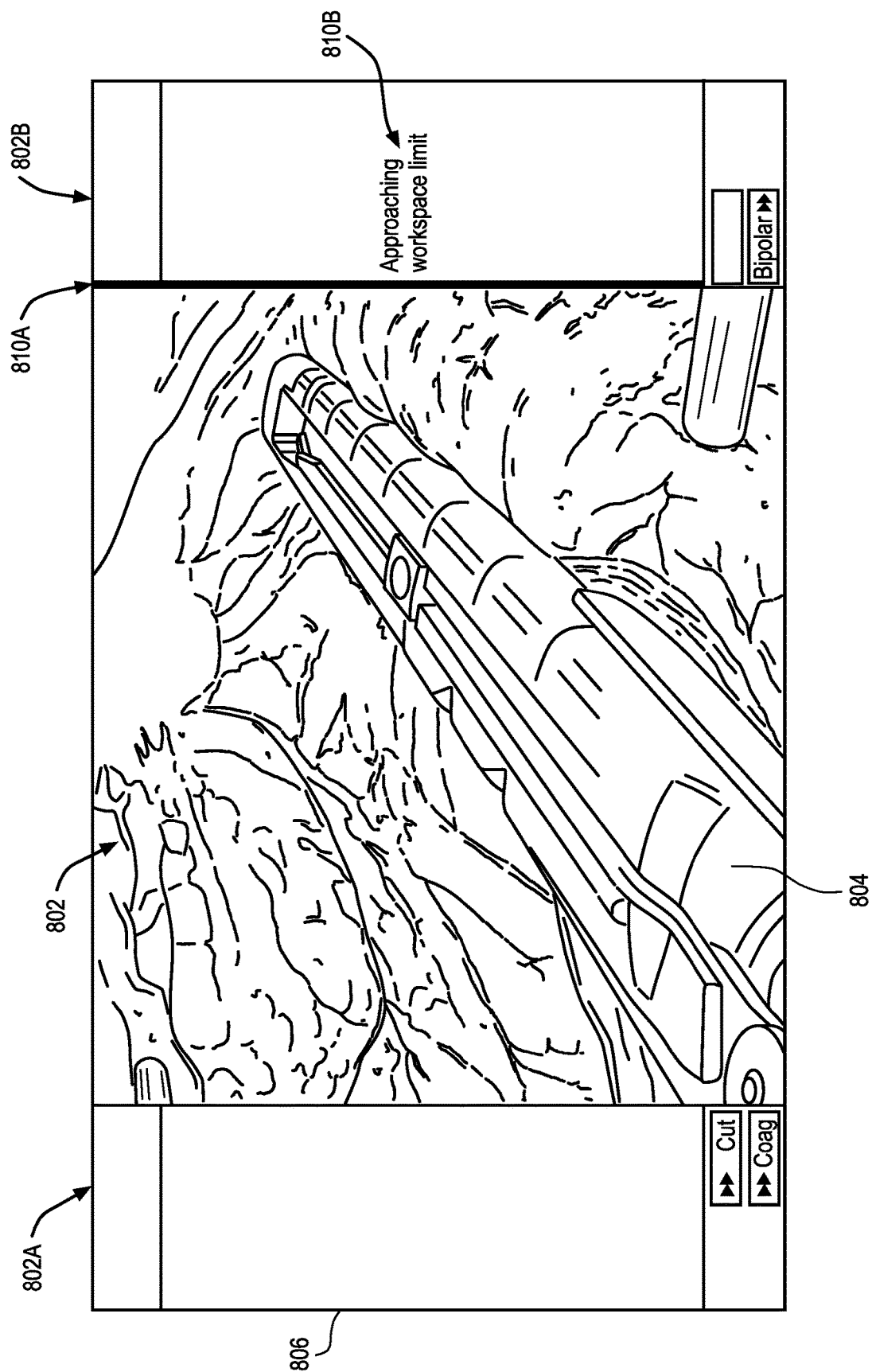

In other aspects, the indicator 808 may, in addition to indicating to the user that the UID is in a warning zone, indicate to the user which UID is within the warning zone and/or which boundary of the warning zone the UID is closest to. For example, FIG. 8B illustrates an indictor 810A that indicates to the surgeon which UID is approaching a workspace boundary or limit. Representatively, in FIG. 8B, display screen 802 is shown having a left side panel 802A and a right side panel 802B. The left side panel 802A may display information relating to a left UID (e.g., a UID held in the left hand), and the right side panel 802B may display information relating to a right UID (e.g., a UID held in the right hand). Accordingly, when the right UID is detected within the warning zone, an indicator 810A will appear in the right side panel 802B, as shown in FIG. 8B. In this aspect, the indicator 810A is shown as a line along the right side panel 802B. The indicator 810A could, however, be any type of shape, image, icon or the like that can be viewed by the user in the right side panel 802B. The surgeon will therefore understand that the UID held in his or her right hand is in the warning zone and nearing the workspace limit. Similarly, although not shown, if the left UID is detected in the warning zone, a similar warning indicator may appear in the left side panel 802B. The indicator 810A may appear in the center of the left or right panels 802A-B, or in any other region of the left or right panels 802A-B that is easily viewed and understood by the surgeon to mean a left and/or right UID is within the warning zone. In addition, in some aspects, the display may also include an indicator 810B including text which also informs the surgeon that the UID is approaching the workspace limit and/or which side of the workspace the UID is near. For example, the indicator 810B may also appear in the right side panel 802B to indicate that the UID is nearing the right boundary of the workspace, and also include text stating that the UID is "Approaching the workspace limit." Although both indicators 810A, 810B are shown in FIG. 8B, it is contemplated that in some aspects, only one of indicators 810A, 810B may be displayed to indicate that a UID is approaching a workspace boundary or limit (i.e., in the warning zone), and which UID (right or left) is approaching the workspace boundary or limit.

In still further aspects, the feedback provided to the user may identify which edge or boundary a UID is closest to. Representatively, FIGS. 9A-9F are schematic illustrations of indicators that may be used to inform the user which edge a UID is closest to. The indicators 902A-F may appear on the display screen, similar to the previously discussed visual indictors. In this aspect, however, the indicators 902A-F illustrates the boundaries or edges 906, 908, 910, 912 of the workspace. Specifically, the workspace is represented by a top edge 906, a right side edge 908, a bottom side edge 910 and a left side edge 912. The edges 906, 908, 910, 912 are understood by the surgeon as corresponding to the top, right, bottom and left sides of the actual workspace limit of the UID being manipulated by the surgeon. Although edges 906, 908, 910, 912 are shown as straight edges (e.g., forming a square) it should be understood that the edges, boundaries and/or limits discussed herein may have other shapes and/or orientations relative to one another so long as they can be understood by the user as representing a workspace boundary or limit. For example, the edges 906, 908, 910, 912 could be curved, or have any other shape. In addition, in some aspects only the edge or a portion of the edge that the UID is closest to could be shown.

The indicators 902A-F further illustrate to the surgeon a UID icon 904 and position icon 914. The UID icon 904 may represent the UID within the workspace and may be any type of icon that the surgeon recognizes as representing a UID within a workspace. The position icon 914 represents the side or edge of the workspace that the UID is closest to. In other words, the warning zone corresponding to, or otherwise defined by, that particular side or edge. The position icon 914 may appear between the UID icon 904 and the workspace edge 906, 908, 910, 912 that the UID is closest to. The position icon 914 may therefore appear when a UID is detected within a warning zone at a particular side or edge. If no UID is detected near a particular side or within a warning zone defined by a particular side or edge, the position icon 914 may disappear or not otherwise be displayed. If no position icon 914 is present, the surgeon will understand this to mean that no UID is within a warning zone or otherwise close to a particular side or edge of the workspace. The UID icon 904 may remain stationary relative to the workspace edges 906, 908, 910, 912.

Figure 9A:
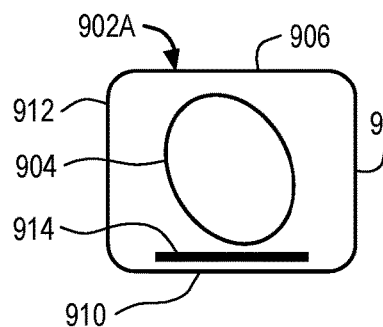
FIGS. 9A-9F provide examples of the visual feedback that may be provided to the user during the Feedback During Usage mode.
Figure 9B:
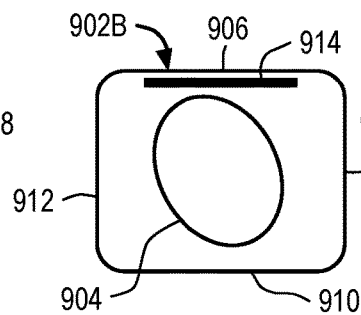
Figure 9C:
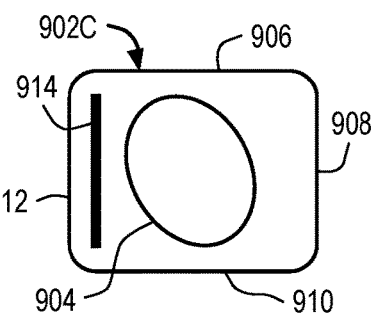
Figure 9D:
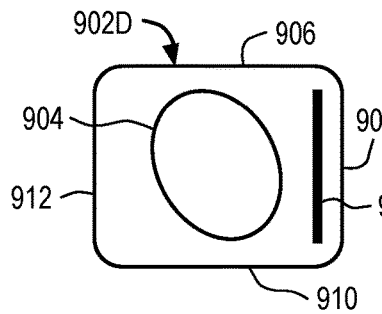

Referring now in more detail to FIG. 9A, FIG. 9A shows an indicator 902A with the position icon 914 displayed near the bottom edge 910 of the workspace. Accordingly, the surgeon will understand that at least one UID being engaged by the surgeon is within the warning zone near the bottom edge of the real workspace. FIG. 9B shows an indicator 902B with the position icon 914 near the top edge 906 of the workspace. Based on the indicator 902B shown in FIG. 9B, the surgeon will understand that at least one UID being engaged by the surgeon is within the warning zone near the top edge of the real workspace. FIG. 9C shows an indicator 902C with the position icon 914 near the left edge 912 of the workspace. Based on the indicator 902C shown in FIG. 9C, the surgeon will understand that at least one UID being engaged by the surgeon is within the warning zone near the left edge of the real workspace. FIG. 9D shows an indicator 902D with the position icon 914 near the right edge 908 of the workspace. Based on the indicator 902D shown in FIG. 9D, the surgeon will understand that at least one UID being engaged by the surgeon is within the warning zone near the right edge of the real workspace.

Figure 9E:
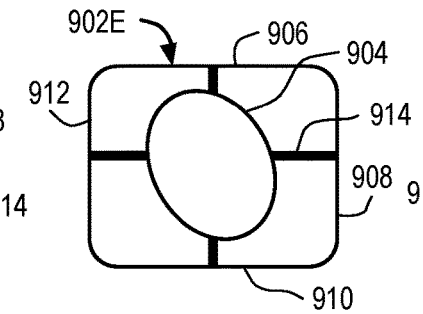
Figure 9F:
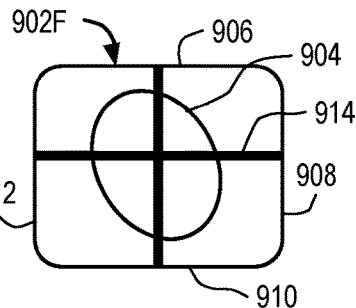

FIG. 9E and FIG. 9F provide additional indicators that illustrate to the surgeon whether they are nearing a front or back edge of the workspace. Representatively, similar to the indicators shown in FIGS. 9A-9D, a position icon 914 is used to indicate which edge the UID is closest to, except in this embodiment, the position icon 914 appears in front of or behind the UID icon 904 to indicate the location of the UID relative to the front or back edge. For example, indicator 902E of FIG. 9E shows the position icon 914 in front of the UID icon 904 to indicate to the user that the UID is close to the front edge (farthest from the user) of the workspace. The indicator 902F of FIG. 9F shows the position icon 914 behind the UID icon 904 to indicate to the user that the UID is close to the back edge (closest to the user) of the workspace. It should be understood that while the position icons 914 are shown in FIGS. 9A-9F as lines or crosses, any shape or size icon suitable for indicating a UID location relative to a boundary may be used.

Figure 10:
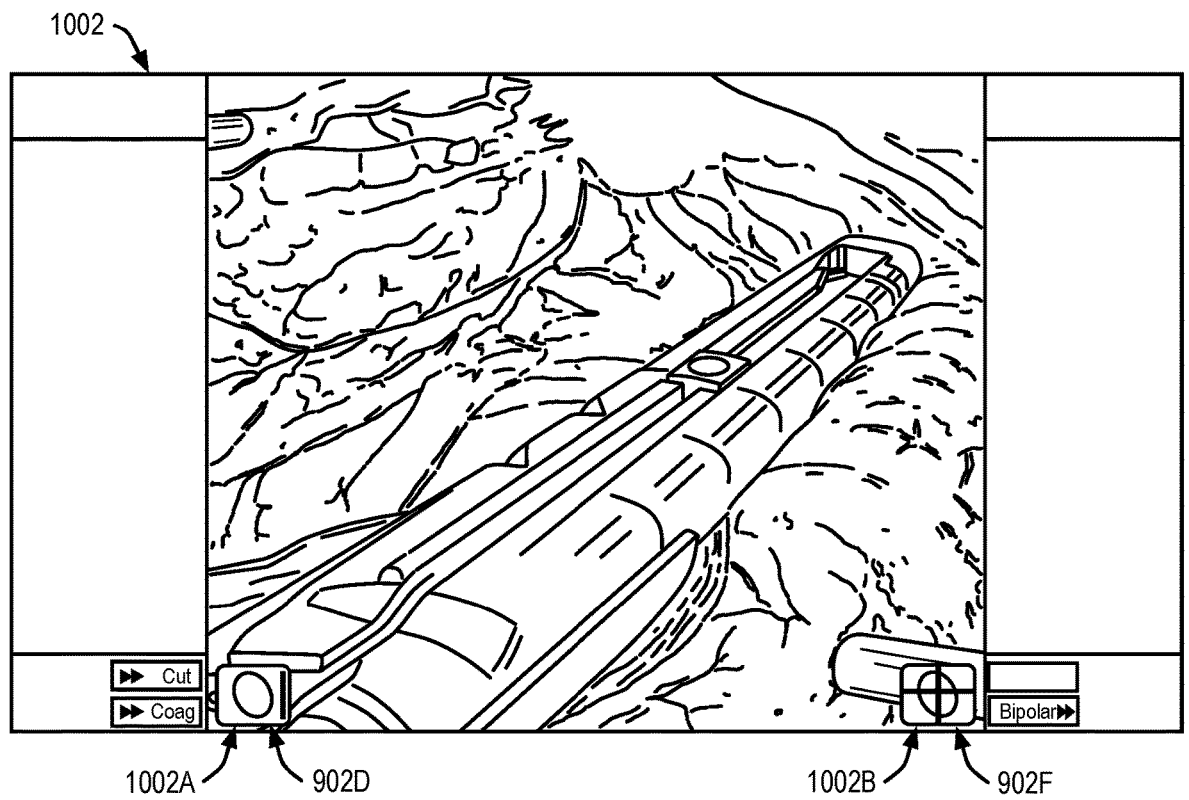
FIG. 10 provides an example of the visual feedback that may be provided to the user during the Feedback During Usage mode.

In some aspects, in addition to indicating to the user that a UID is closest to a particular side, the system may also indicate visually to the user which UID (e.g., right or left UID) is closest to the particular side. FIG. 10 provides a schematic illustration of one such indicator. Representatively, FIG. 10 shows the previously discussed indicators 902D and 902F described in reference to FIG. 9D and FIG. 9F, displayed on the display screen 1002 that is viewed by the user. In addition, FIG. 10 illustrates whether the left or right UID is at the location represented by indicators 902D, 902F based on the position of the indicators 902D, 902F on the screen. In particular, the indicator may be positioned in the bottom left corner 1002A of the screen to indicate the left UID position and the indicator may be positioned in the bottom right corner 1002B of the screen to indicate the right UID position. For example, indicator 902D is positioned at the bottom left corner 1002A of the display screen 1002 to indicate to the user that the left UID is close to the right edge of the workspace. Indicator 902F is positioned at the bottom right corner 1002B of the display screen 1002 to indicate to the user that the right UID is close to the back edge of the workspace. Although indicators 902D and 902F are illustrated in FIG. 10, it should be understood that any one or more of indicators 902A-F described in FIGS. 9A-F may be displayed in the corners 1002A-B to indicate whether a right or left UID is at the indicated location. Similar to the previously discussed feedback operations, if none of indicators 902A-F are displayed in the corners 1002A-B, this means that no UID is within a warning zone or otherwise approaching a workspace limit.

Figure 11:
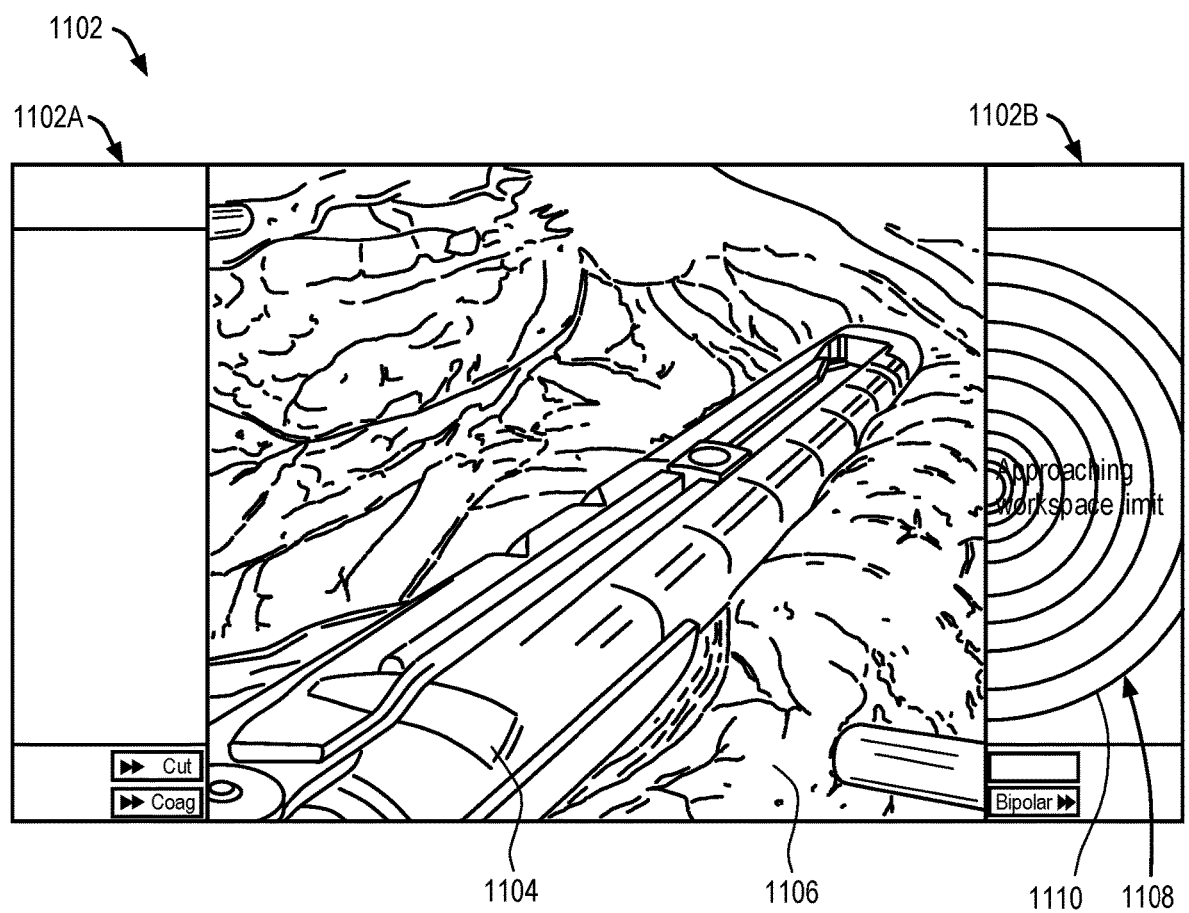
FIG. 11 provides an example of the visual feedback that may be provided to the user during the Feedback During Usage mode.

FIG. 11 provides an additional visual feedback indicator that may be provided to the user during the Feedback During Usage mode to indicate to the surgeon whether they are nearing, meeting and/or exceeding a workspace limit. Representatively, FIG. 11 illustrates a display screen 1102 that the surgeon can use to view the movement of a surgical instrument 1104 they are controlling with the UID during a surgical procedure on a patient 1106. The display screen 1102 further includes a left panel 1102A and a right panel 1102B that may be used to display an indicator 1108. In some aspects, the panels 1102A and 1102B may also correspond to a particular left or right UID. For example, the left panel 1102A may correspond to a left UID and the right panel 1102B may correspond to a right UID. Accordingly, if the indicator 1108 is in the right panel 1102B as shown, the user will understand that the indicator 1108 is providing information about the right UID in the user's right hand. Similarly, if the indicator 1108 is in the left penal 1102A, the user will understand that the indicator 1108 is providing information about the left UID in the user's left hand. Similar to the previously discussed indicators, indicator 1108 indicates to the user whether they are nearing a workspace limit. Indicator 1108 in this aspect, however, is shown as a series of concentric circles or rings 1110. The intensity of the circles or rings 1110 change based on a distance between the UID and the workspace limit or boundary. For example, the circles or rings 1110 grow outwardly to the right side of the display 1102 as the UID gets closer to the workspace limit. FIG. 11 shows the circles or rings 1110 extending all the way to the right side of panel 1102B. Accordingly, the user would understand this to mean that the UID in the user's right hand has reached the workspace limit, and is possibly exceeding the workspace limit or boundary. Since the UID is no longer within the workspace boundaries, the UID is no longer operable to control the surgical instrument. On the other hand, if only a single ring 1110 near the left side of the panel 1102B is shown, this indicates to the user that the user has moved the UID within the warning zone, but the UID is still relatively far from the workspace limit. If the user continues to move the UID in the same direction, however, the intensity (e.g., number) of the rings 1110 will increase indicating to the user that they are getting closer to the workspace limit. The user can therefore adjust the movement of the UID to ensure they remain within the workspace limit.

Figure 12:
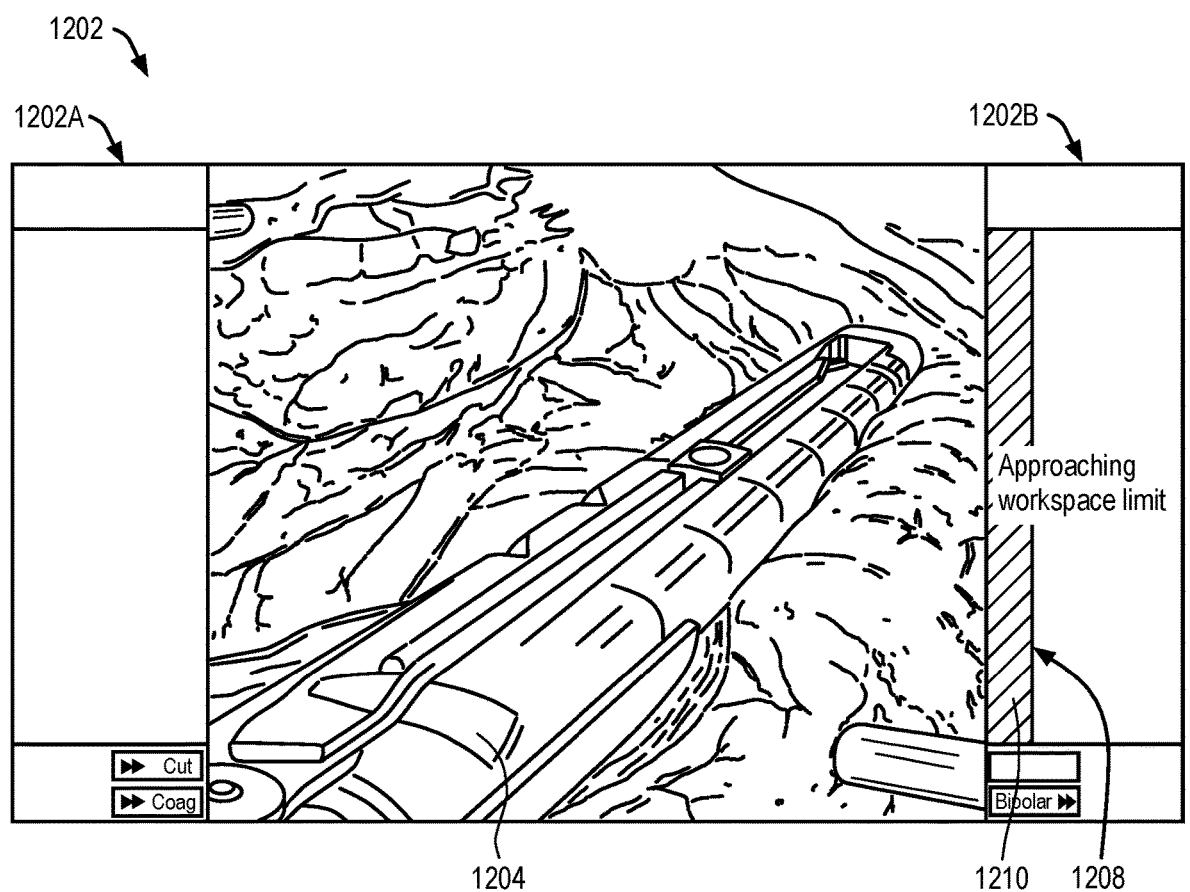
FIG. 12 provides an example of the visual feedback that may be provided to the user during the Feedback During Usage mode.

FIG. 12 provides an additional visual feedback indicator that may be provided to the user during the Feedback During Usage mode to indicate to the surgeon whether they are nearing, meeting and/or exceeding a workspace limit. Representatively, FIG. 12 illustrates a display screen 1202 that the surgeon can use to view the movement of a surgical instrument 1204 they are controlling with the UID during a surgical procedure on a patient 1206. The display screen 1202 further includes a left panel 1202A and a right panel 1202B that may be used to display an indicator 1208. The panels 1202A and 1202B may also correspond to a particular left or right UID, as previously discussed. Indicator 1208 may be displayed in one or more of panels 1202A-B to indicate whether the right or left UID is nearing, meeting and/or exceeding a workspace limit. In this aspect, however, indicator 1208 is shown as a bar 1210 that changes in size depending on a distance between the UID and the workspace limit or boundary. For example, the bar 1210 grows outwardly to the right side of the display 1202 as the UID gets closer to the workspace limit. FIG. 12 shows the bar 1210 extending less than halfway to the right side of panel 1202B. Accordingly, the user would understand this to mean that the UID in the user's right hand is in the warning zone, but is still closer to the operable workspace than the workspace limit or boundary beyond which operation of the associated surgical component is not allowed. On the other hand, if the bar 1210 were to reach all the way to the right side of panel 1202B, this indicates to the user that the user has reached or exceeded the workspace limit and the UID is no longer operable to control the surgical instrument. The user can therefore adjust the movement of the UID to ensure they remain within the workspace limit.

Figure 13:
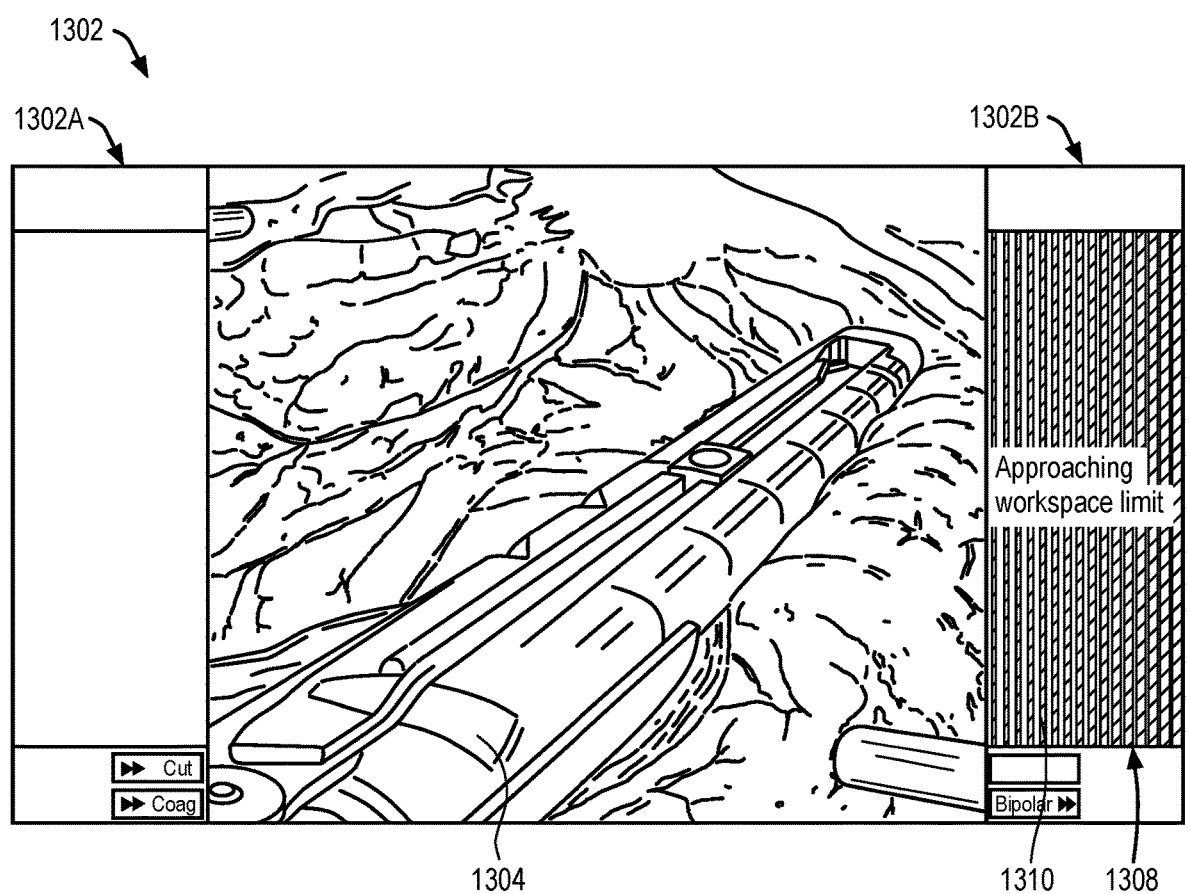
FIG. 13 provides an example of the visual feedback that may be provided to the user during the Feedback During Usage mode.

FIG. 13 provides an additional visual feedback indicator that may be provided to the user during the Feedback During Usage mode to indicate to the surgeon whether they are nearing, meeting and/or exceeding a workspace limit. Representatively, FIG. 13 illustrates a display screen 1302 that the surgeon can use to view the movement of a surgical instrument 1304 they are controlling with the UID during a surgical procedure on a patient 1306. The display screen 1302 further includes a left panel 1302A and a right panel 1302B that may be used to display an indicator 1308. The panels 1302A and 1302B may also correspond to a particular left or right UID, as previously discussed. Indicator 1308 may be displayed in one or more of panels 1302A-B to indicate whether the right or left UID is nearing, meeting and/or exceeding a workspace limit. In this aspect, however, indicator 1308 is shown as a series of lines 1310 that increase or decrease in number depending on a distance between the UID and the workspace limit or boundary. For example, the series of lines 1310 increase in number outwardly to the right side of the display 1302 as the UID gets closer to the workspace limit. FIG. 13 shows the series of lines 1310 extending all the way to the right side of panel 1302B. Accordingly, the user will understand this to mean that the UID held in the user's right hand has met and/or exceeded the workspace limit and the UID is no longer operable to control the surgical instrument. The user can therefore adjust the movement of the UID to ensure they remain within the workspace limit. Alternatively, if only one or two lines 1310 are shown, the user will understand this to mean that the UID in the user's right hand is in the warning zone, but is still closer to the operable workspace than the workspace limit or boundary beyond which operation of the associated surgical component is not allowed.

Figure 14A:
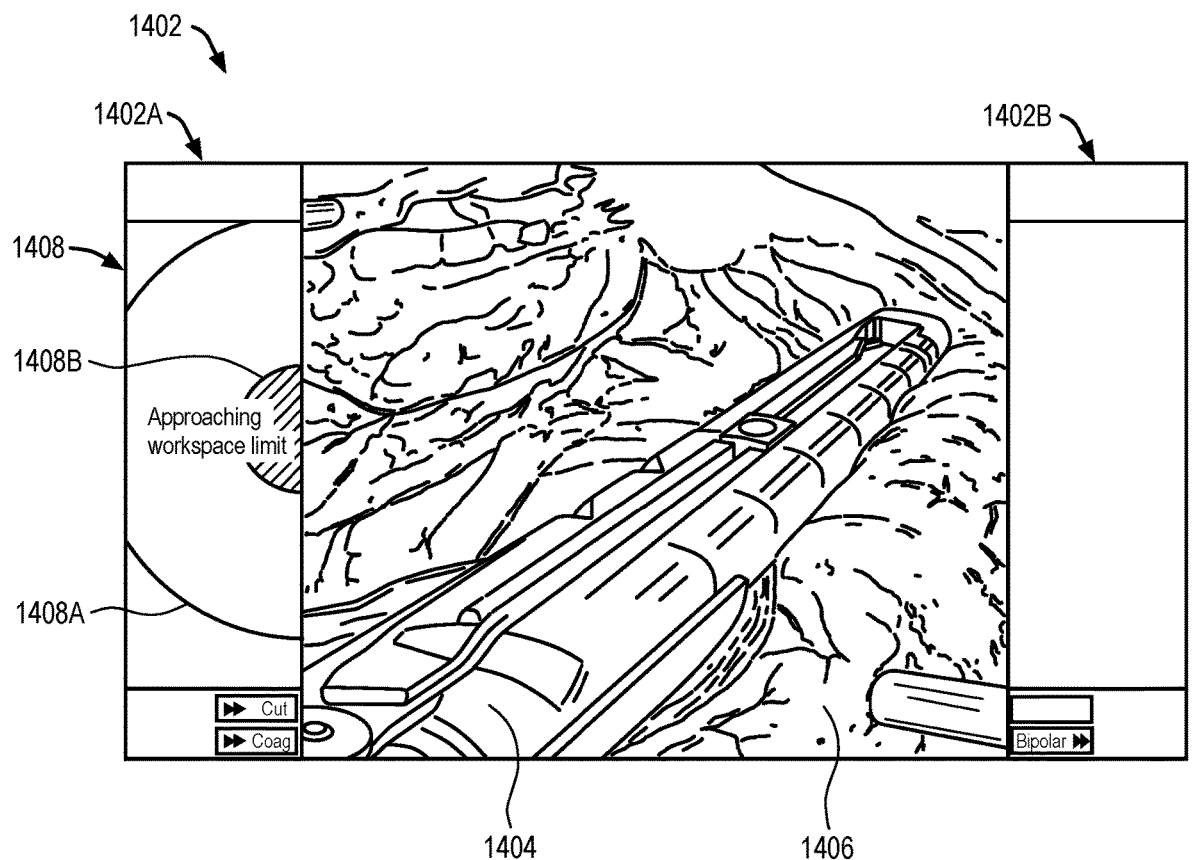
FIGS. 14A-14B provide examples of the visual feedback that may be provided to the user during the Feedback During Usage mode.
Figure 14B:
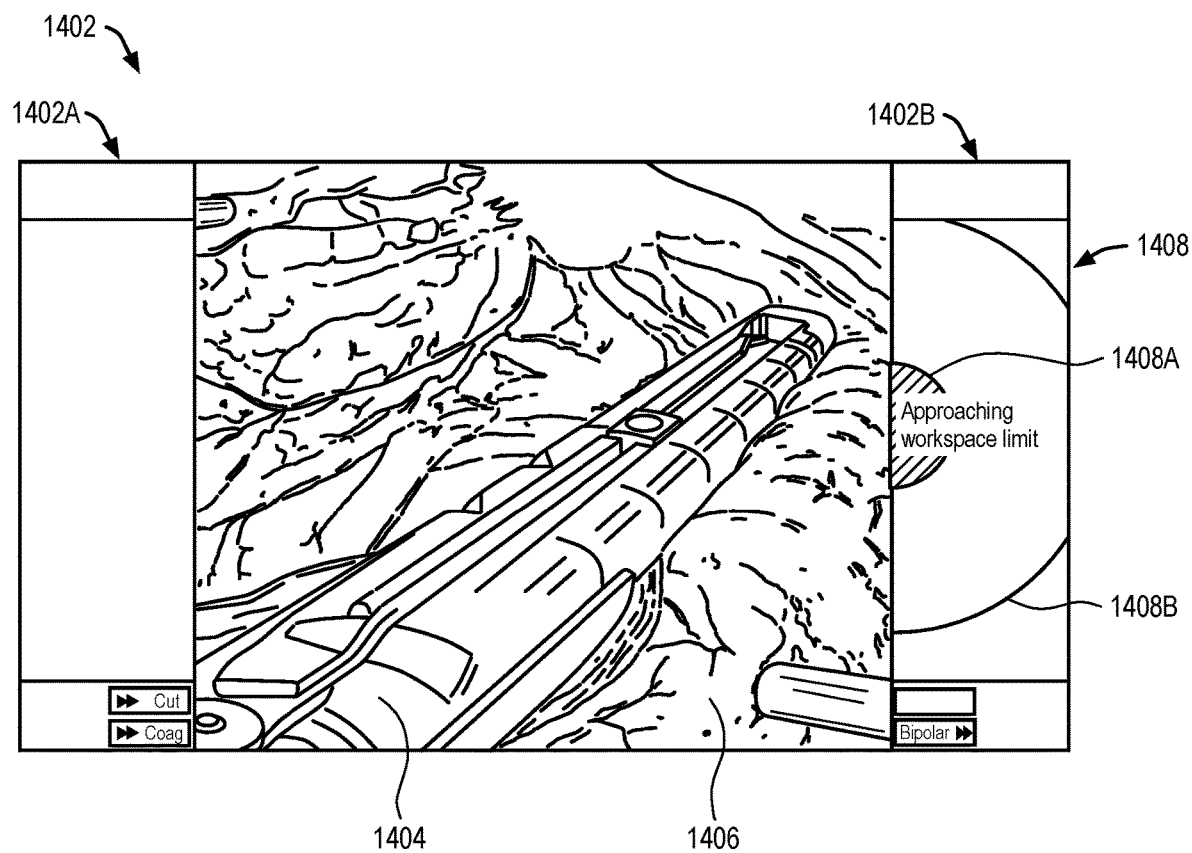

FIG. 14A and FIG. 14B illustrate additional visual feedback indicators that may be provided to the user during the Feedback During Usage mode to indicate to the surgeon which workspace boundary they are closest to. Similar to the previously discussed configurations, FIG. 14A-B include a display screen 1402 that the surgeon can use to view the movement of a surgical instrument 1404 they are controlling with the UID during a surgical procedure on a patient 1406. The display screen 1402 further includes a left panel 1402A and a right panel 1402B that may be used to display an indicator 1408. In this configuration, however, panels 1402A-B are used to represent a left or right edge of the workspace limit, instead of a left or right UID. Representatively, the left side panel 1402A represents the left edge or boundary of the workspace limit. The right side panel 1402B represents the right edge or boundary of the workspace limit. Accordingly, if indicator 1408 appears in the left side panel 1402A as shown in FIG. 14A, the UID is nearing the left edge of the workspace boundary. On the other hand, if indicator 1408 appears in the right side panel 1402B as shown in FIG. 14B, the UID is nearing the left edge of the workspace boundary. The UID nearing the workspace limit could be the right or left UID. Similar to the previously discussed indicators, indicator 1408 also indicates to the user how close they are getting to the workspace limit. In particular, indicator 1408 includes an inner circle 1408A and an outer circle 1408B that represents the left edge of the workspace limit. The inner circle 1408A expands or contracts depending on how close the UID is to the left edge of the workspace limit. For example, as the UID gets closer to the left edge of the workspace limit, the inner circle 1408A expands and gets closer to the outer circle 1408B. If the inner circle 1408A reaches the outer circle 1408B, the left edge of the workspace limit has been exceeded.

Figure 15A:
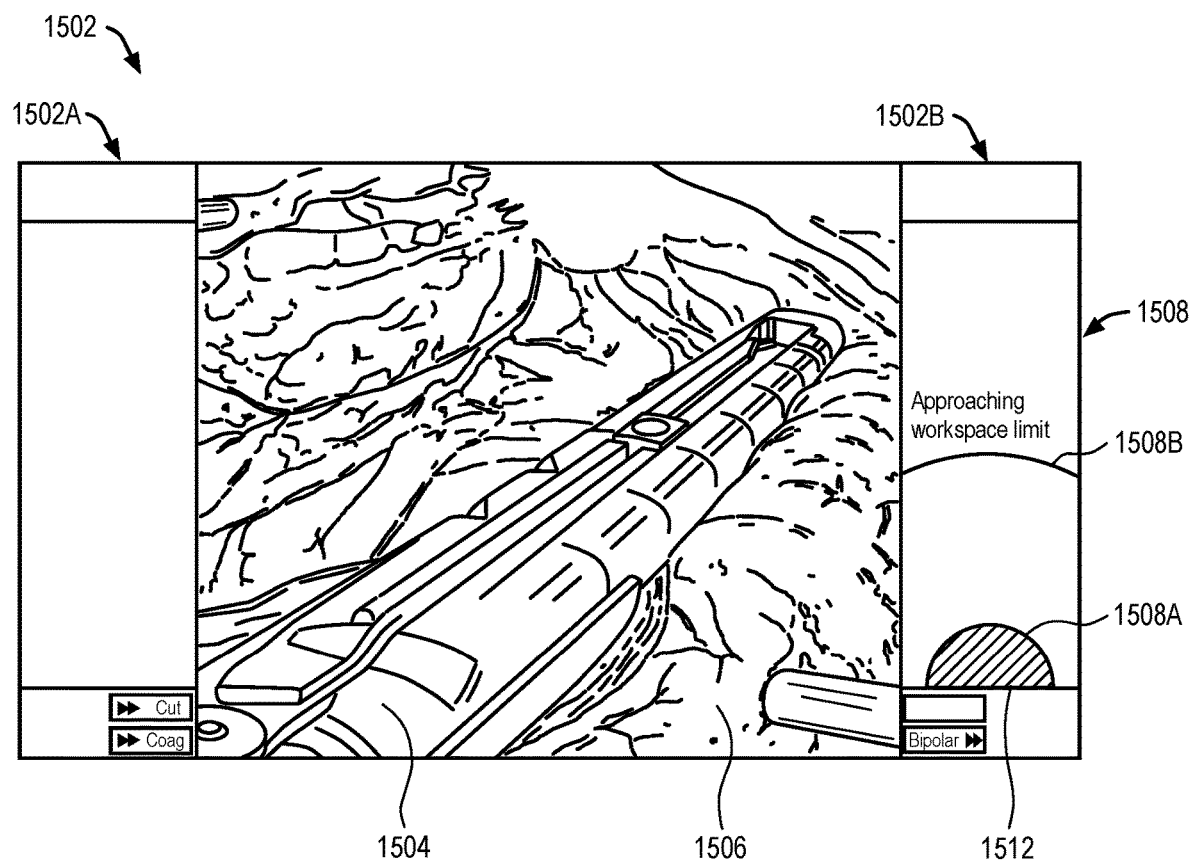
FIGS. 15A-15B provide examples of the visual feedback that may be provided to the user during the Feedback During Usage mode.
Figure 15B:
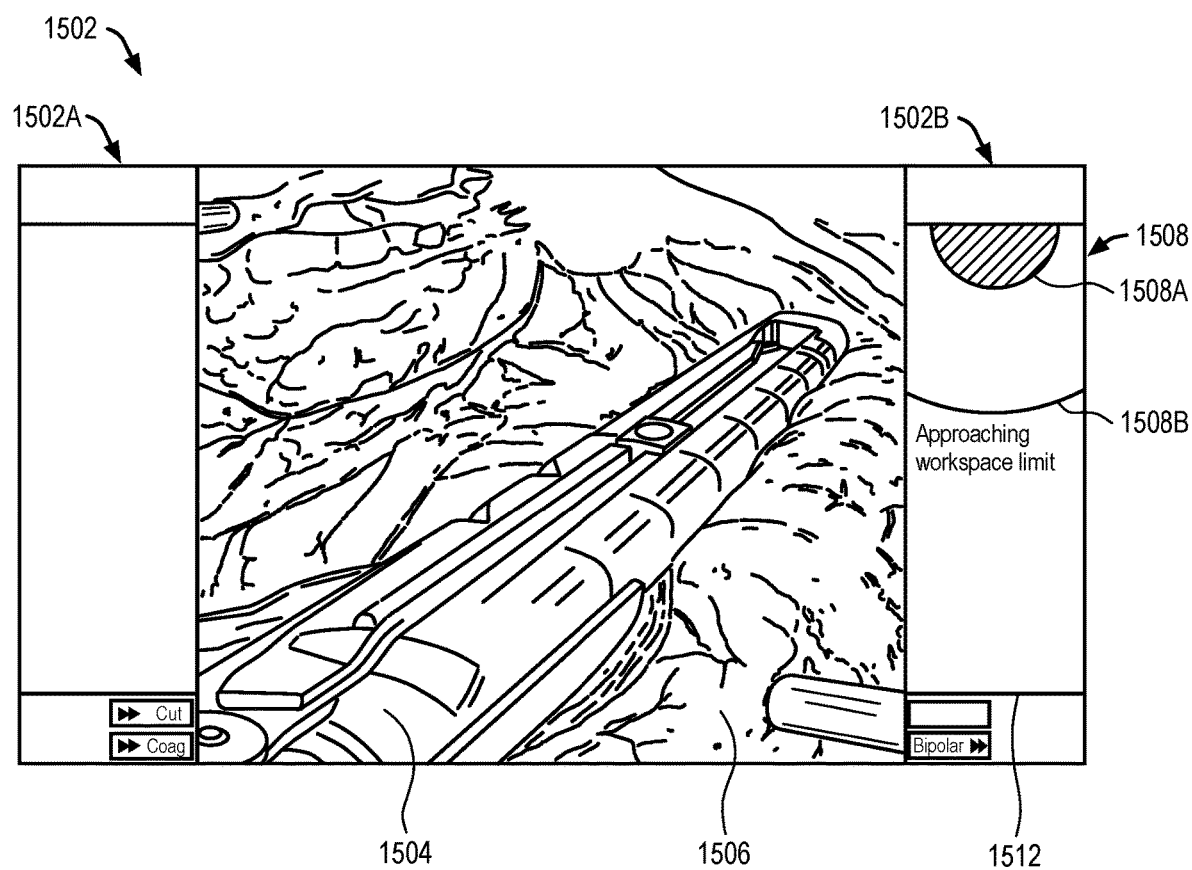

FIG. 15A and FIG. 15B illustrate additional visual feedback indicators that may be provided to the user during the Feedback During Usage mode to indicate to the surgeon which workspace boundary they are closest to. Similar to the previously discussed configurations, FIG. 15A-B include a display screen 1502 that the surgeon can use to view the movement of a surgical instrument 1504 they are controlling with the UID during a surgical procedure on a patient 1506. The display screen 1502 further includes a left panel 1502A and a right panel 1502B that may be used to display an indicator 1508. In this configuration, however, panels 1502A-B are used to represent a left or right UID and the indicator 1508 is positioned within the panel in way that indicates whether the UID is nearing a top or bottom edge of the workspace boundary. Representatively, the left side panel 1502A provides information about a left UID and the right side panel 1502B provides information about a right UID. In addition, the indicator 1508 moves toward or away from the top side 1510 and/or the bottom side 1512 of the panels 1502A-B to further indicate whether the UID is nearing the top or bottom edge of the workspace boundary. In addition, similar to the previously discussed indicators, indicator 1508 also indicates to the user how close the UID is getting to the workspace limit. In particular, indicator 1508 includes an inner circle 1508A and an outer circle 1508B that represents the top or bottom edge of the workspace limit. The inner circle 1508A expands or contracts depending on how close the UID is to the top or bottom edge of the workspace limit.

For example, FIG. 15A shows indicator 1508 within the right panel 1502B of display 1502. Accordingly, indicator 1508 represents that the right UID is within a warning zone of a workspace boundary. In addition, the outer circle 1508B displayed above the inner circle 1508A means that the UID (represented by inner circle 1508A) is nearing the top edge of the workspace boundary or limit. In other words, the UID is within the warning zone defined by the top edge of the workspace boundary or limit. To further indicate to the user how close they are to the top edge of the workspace limit, the inner circle 1408A can expand or contract as previously discussed. For example, as the UID gets closer to the top edge of the workspace limit (e.g., moves toward the top side 1510 of panel 1502B), the inner circle 1508A expands and gets closer to the outer circle 1508B. If the inner circle 1508A reaches the top of the outer circle 1508B, the top edge of the workspace limit has been exceeded.

Similar to FIG. 15A, FIG. 15B shows indicator 1508 within the right panel 1502B of display 1502. Accordingly, indicator 1508 represents that the right UID is within a warning zone of a workspace boundary. In addition, the outer circle 1508B displayed below the inner circle 1508A means that the UID (represented by inner circle 1508A) is nearing the bottom edge of the workspace boundary or limit. In other words, the UID is within the warning zone defined by the bottom edge of the workspace boundary or limit. To further indicate to the user how close they are to the bottom edge of the workspace limit, the inner circle 1408A can expand or contract as previously discussed. For example, as the UID gets closer to the bottom edge of the workspace limit (e.g., moves toward the bottom side 1512 of panel 1502B), the inner circle 1508A expands and gets closer to the outer circle 1508B. If the inner circle 1508A reaches the bottom of the outer circle 1508B, the bottom edge of the workspace limit has been exceeded.

Figure 16A:
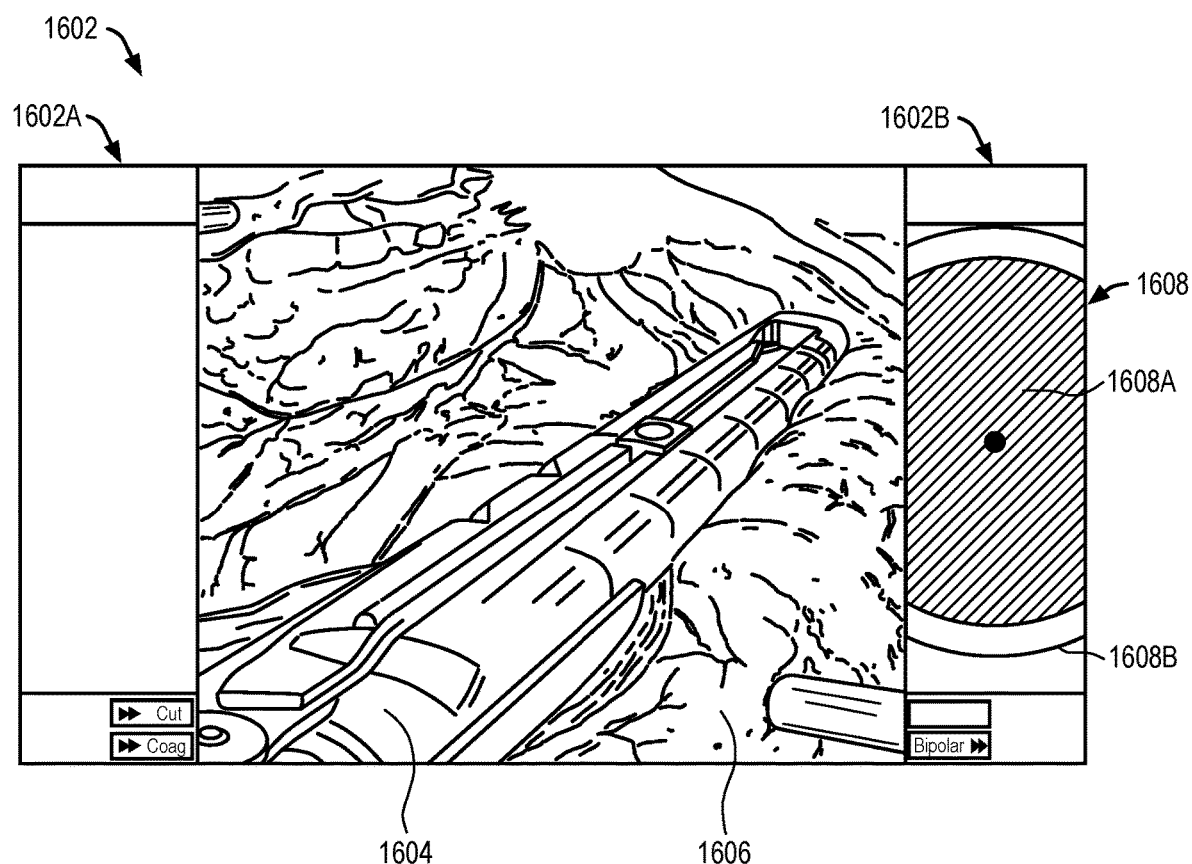
FIGS. 16A-16B provide examples of the visual feedback that may be provided to the user during the Feedback During Usage mode.
Figure 16B:
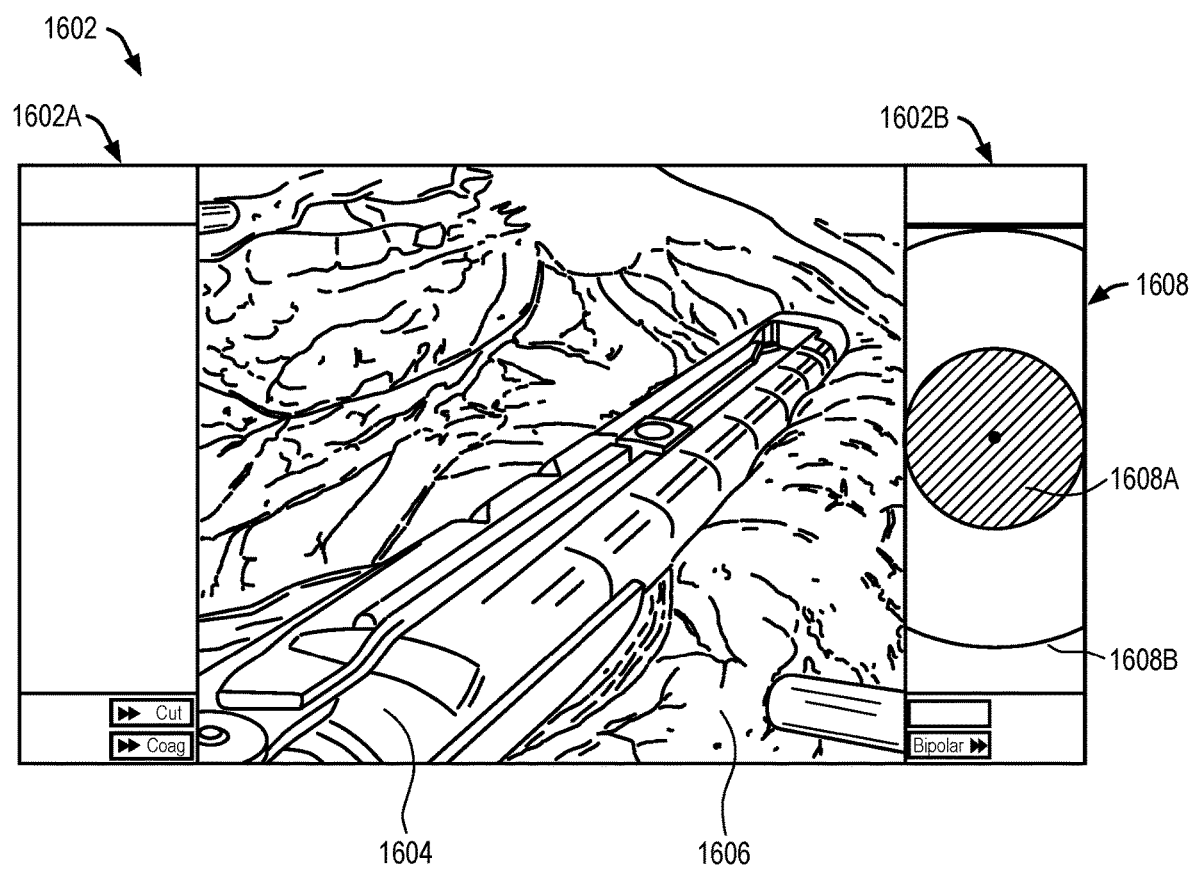

FIG. 16A and FIG. 16B illustrate additional visual feedback indicators that may be provided to the user during the Feedback During Usage mode to indicate to the surgeon which workspace boundary they are closest to. In addition, the indicator shown in FIGS. 16A-B identifies to the user which UID is closest to the boundary or limit. Similar to the previously discussed configurations, FIG. 16A-B include a display screen 1602 that the surgeon can use to view the movement of a surgical instrument 1604 they are controlling with the UID during a surgical procedure on a patient 1606. The display screen 1602 further includes a left panel 1602A and a right panel 1602B that may be used to display an indicator 1608. In this configuration, however, panels 1602A-B are used to represent a left or right UID and the indicator 1608 is positioned within the panel in way that indicates whether the UID is nearing a top or bottom edge of the workspace boundary. Representatively, the left side panel 1602A provides information about a left UID and the right side panel 1602B provides information about a right UID.

In addition, the indicator 1608 includes an icon that represents movement in or out of page to further indicate whether the UID is nearing the back edge or front edge of the workspace boundary. In particular, indicator 1608 includes an inner icon 1608A and an outer icon 1608B. The inner icon 1608A represents the proximity of the UID to the workspace boundary (or edge) and the outer icon 1608B represents the boundary (or edge). The inner icon 1608A changes in size relative to the outer icon 1608B to represent movement of the UID relative to the workspace boundary (e.g., movement toward or away from the boundary). For example, if the inner icon 1608A fills in the area defined by the outer boundary 1608B, this indicates the UID is at the workspace limit. On the other hand, if the inner icon 1608A does not fill in the area defined by the outer boundary 1608B, the UID has not yet reached the workspace limit. In this aspect, the indicator 1608 also indicates to the user how close they are to the workspace boundary or limit.

For example, FIG. 16A shows indicator 1608 within the right panel 1602B of display 1602. Accordingly, indicator 1608 represents that the right UID is within a warning zone of a workspace boundary. In addition, indicator 1608 represents that the right UID is within the warning zone at the back edge of the workspace, or close to the back edge. In particular, in this aspect, to represent that the right UID is close to the back edge (e.g., the edge closest to the user), the inner icon 1608A (e.g., the shaded space) fills in the entire area within the outer icon 1608B (e.g., the white space). The user will understand this illustration as corresponding to the real life UID movement because as the user moves or pulls a UID closer to them during a procedure (e.g., closer to the back edge of the workspace), the UID will appear to increase in size. This apparent increase in size corresponds to the inner icon 1608A increasing in size and filling in the space defined by the outer icon 1608B. On the other hand, when the inner icon 1608A does not fill in the entire area within the outer icon 1608B as shown in FIG. 16B, this represents that the UID is closer to the front edge (e.g., the edge farthest from the user). The user will understand this illustration as corresponding to the real life UID movement because as the user moves the UID away from them during a procedure (e.g., closer to the front edge of the workspace), the UID will appear to decrease in size. In addition, in some aspects, the proximity of the outer edge of the inner icon 1608A relative to the outer edge of the outer icon 1608B may further indicate to the user how close they are to the back edge or the front edge. For example, where the outer edge of the inner icon 1608A is at the outer edge of the outer icon 1608B (e.g., the outer icon 1608B in FIG. 16A is no longer visible), the UID has reached or exceeded the back edge workspace limit. If, on the other hand, the outer edge of the inner icon 1608A is close to the outer edge of the outer edge of the outer icon 1608B, but is not at the outer edge of the outer icon 1608B, the UID is close to the back edge of the workspace limit but has not reached or exceeded the limit.

FIGS. 17A-17J illustrate additional visual feedback indicators that may be provided to the user during the Feedback During Usage mode to indicate to the surgeon which workspace boundary they are closest to. Representatively, FIGS. 17A-17J show indicators 1708 in which the workspace boundaries or limits are illustrated as sides or edges 1702A, 1702B, 1702C and 1702D. For example, a top edge 1702A, a right edge 1702B, a bottom edge 1702C and a left edge 1702D. The indicator 1708 further includes a first icon 1708A and a second icon 1708B which change in size, shape and/or orientation relative to the edges 1702A-D to illustrate which edge, limit, boundary and/or warning zone of the workspace the UID is closest to.

Representatively, FIG. 17A shows first icon 1708A is increasing in size (e.g., increasing in thickness or width) toward the right edge 1702B. For example, first icon 1708A is almost as thick or wide as second icon 1708B. Said another way, the right side of the first icon 1708A is getting closer to the right edge 1702B, and in turn, the second icon 1708B is getting smaller. This illustration is intended to simulate a real movement of the UID by the surgeon to the right or toward a right side of the workspace (e.g., the UID gets closer to the right edge). The user will therefore understand from the indicator 1708 of FIG. 17A that the UID is close to hitting the right edge, but has not yet reached the right edge boundary.

FIG. 17B shows first icon 1708A with an even greater size increase toward the right edge 1702B (e.g., first icon 1708A is now bigger than second icon 1708B). The user will therefore understand from the indicator 1708 of FIG. 17B that the UID is even closer to hitting the right edge of the workspace boundary then in FIG. 17A.

FIG. 17C shows first icon 1708A increasing in size toward the left edge 1702D. For example, FIG. 17C can be understood as showing that the left side of the first icon 1708A is getting closer to the left edge 1702D, and the second icon 1708B is therefore decreasing in size. The user will therefore understand from the indicator 1708 of FIG. 17C that the UID is close to hitting the left edge, but has not yet reached the right edge boundary.

FIG. 17D shows first icon 1708A increasing in size toward the bottom edge 1702B. For example, FIG. 17D can be understood as showing that the bottom side of the first icon 1708A is getting closer to the bottom edge 1702B, and the second icon 1708B is therefore decreasing in size. The user will therefore understand from the indicator 1708 of FIG. 17 that the UID is close to hitting the bottom edge, but has not yet reached the bottom edge boundary.

FIG. 17E shows first icon 1708A increasing in size toward the top edge 1702A. For example, FIG. 17E can be understood as showing that the top side of the first icon 1708A is getting closer to the top edge 1702A, and the second icon 1708B is therefore decreasing in size. The user will therefore understand from the indicator 1708 of FIG. 17E that the UID is close to hitting the top edge, but has not yet reached the right edge boundary.

FIG. 17F represents a UID nearing the front or back edge of the workspace limit. In this aspect, the first icon 1708A is shown in the center of the second icon 1708B. The first icon 1708A will increase and/or decrease in size depending on whether the UID is closer to the front or back edge of the workspace limit. For example, if the UID is nearing the front edge of the workspace limit (e.g., edge farthest from the user), the first icon 1708A may decrease in size to represent the UID moving away from the user. If, on the other hand, the UID is nearing the back edge of the workspace limit (e.g., edge closest to the user), the first icon 1708A may increase in size to represent the UID moving toward the user.

FIG. 17G-J are similar to FIG. 17A-F, however, in these figures, the proximity of the UID to more than one side is illustrated. For example, FIG. 17G represents a UID approaching both the right and bottom edge of the workspace. Representatively, the first icon 1708A is shown increasing in size toward, or having boundary moving toward, both the right edge 1702B and the bottom edge 1702C of the workspace. This therefore simulates the movement of a UID by the surgeon toward the right and bottom edges of the real workspace.

FIG. 17H represents a UID approaching a bottom edge and a front edge or a back edge of the workspace. Representatively, first icon 1708A is shown increasing in size toward, or having a boundary moving toward, the bottom edge 1702C, similar to FIG. 17D. In addition, first icon 1708A includes a portion in the center of the second icon 1708B to represent the UID moving toward the front or back edge, similar to FIG. 17F.

FIG. 17I represents a UID approaching a right edge and a front edge or a back edge of the workspace. Representatively, first icon 1708A is shown increasing in size toward, or having a boundary moving toward, the right edge 1702B, similar to FIG. 17A-B. In addition, first icon 1708A includes a portion in the center of the second icon 1708B to represent the UID moving toward the front or back edge, similar to FIG. 17F.

FIG. 17J represents a UID approaching a right edge, a bottom edge and a front edge or a back edge of the workspace. Representatively, first icon 1708A is shown increasing toward, or having a boundary moving toward, the right edge 1702B, similar to FIG. 17A-B. In addition, first icon 1708A is shown increasing in size toward, or having a boundary moving toward, the bottom edge 1702C, similar to FIG. 17D. In addition, first icon 1708A includes a portion in the center of the second icon 1708B to represent the UID moving toward the front or back edge, similar to FIG. 17F.

FIGS. 18A-H illustrate additional visual feedback indicators that may be provided to the user during the Feedback During Usage mode to indicate to the surgeon which workspace boundary they are closest to, a relative distance to a boundary and/or which UID is close to the boundary. Representatively, FIGS. 18A-H show indicators 1808 in which the workspace boundaries or limits are illustrated as sides or edges 1802A, 1802B, 1802C and 1802D. For example, a top edge 1802A, a right edge 1802B, a bottom edge 1802C and a left edge 1802D. The indicator 1808 further includes a first icon 1808A which moves relative to a second icon 1808B and the edges 1802A-D to illustrate which edge, limit, boundary and/or warning zone of the workspace the UID is closest to. In addition, the first and second icons 1808A-B may change in size relative to the workspace boundaries 1802A-C to indicate which edge, limit, boundary and/or warning zone of the workspace the UID is closest to. In addition, the icons can indicate the UID distance to a boundary and/or which UID is closest to the boundary.

Figure 18A:
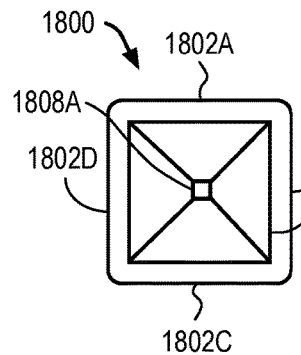
FIGS. 18A-18H provide examples of the visual feedback that may be provided to the user during the Feedback During Usage mode.

Representatively, FIG. 18A represents a UID that has just entered a warning zone. In this aspect, FIG. 18A shows first icon 1808A as a small square within the center of second icon 1808B. The second icon 1808B is also a square, but is much larger and almost at boundaries 1802A-C.

Figure 18B:
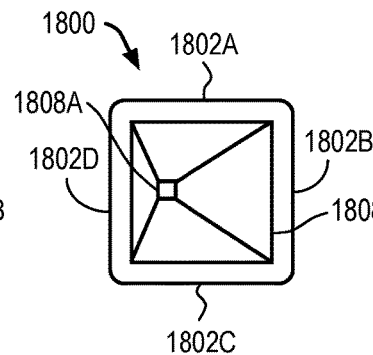

FIG. 18B represents a UID that is nearing the left edge of the workspace. In this aspect, FIG. 18B shows the first icon 1808A closest to the left side 1802D, with the first and second icons 1808A-B remaining the same size.

Figure 18C:
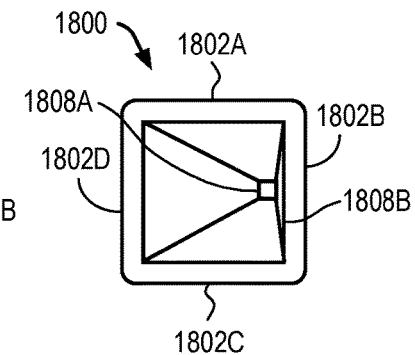

FIG. 18C represents a UID that is at the right edge of the workspace. In this aspect, FIG. 18C shows the first icon 1808A touching the right side 1802B, with the first and second icons 1808A-B remaining the same size.

Figure 18D:
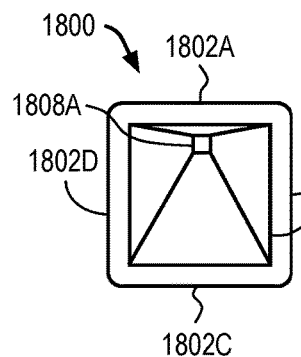

FIG. 18D represents a UID that is nearing the top edge of the workspace. In this aspect, FIG. 18D shows the first icon 1808A nearing the top side 1802A, with the first and second icons 1808A-B remaining the same size.

Figure 18E:
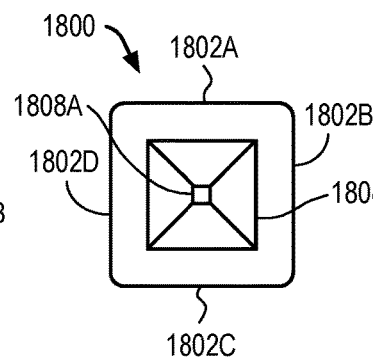

FIG. 18E represents a UID that is nearing the front edge of the workspace. In this aspect, FIG. 18E shows the first icon 1808A in the center of the second icon 1808B, and the first icon 1808A decreases in size indicating that it is near, or nearing, the front edge (e.g., the UID is moving away from the user). The second icon 1808A remains the same size.

Figure 18F:
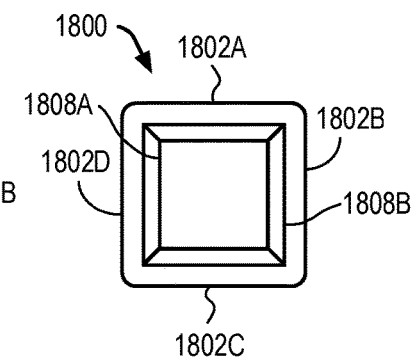

FIG. 18F represents a UID that is nearing the back edge of the workspace. In this aspect, FIG. 18F shows the first icon 1808A in the center of the second icon 1808B, and the first icon 1808A increases in size indicating it is near, or nearing, the back edge (e.g., the UID is moving towards the user). The second icon 1808B remains the same size.

Figure 18G:
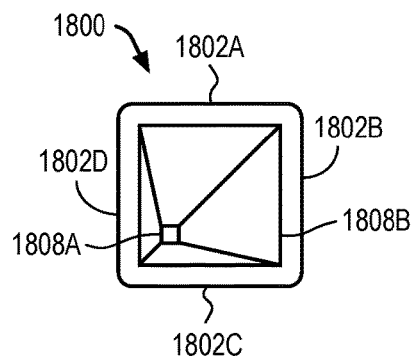

FIG. 18G represents a UID that is nearing the left edge, bottom edge and front edge of the workspace. In this aspect, FIG. 18G shows the first icon 1808A nearing the left side 1802D and the bottom side 1802C. In addition, the first icon 1808A decreases in size relative to the second icon 1808B (which remains the same size), similar to FIG. 18E. Thus, FIG. 18G also indicates movement toward the front edge (e.g., the UID is moving away from the user).

Figure 18H:
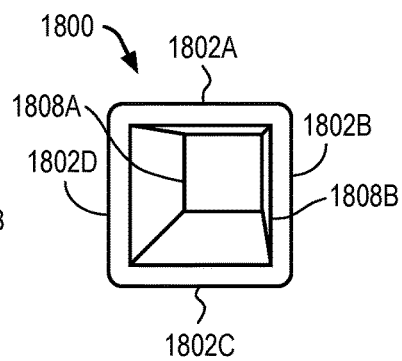

FIG. 18H represents a UID that is nearing the right and back edges of the workspace. In this aspect, FIG. 18H shows the first icon 1808A nearing the right side 1802B and increasing in size relative to second icon 1808B to represent the UID nearing the back edge. The second icon 1808B remains the same size.

In addition, is contemplated that in some aspects, the visual feedback may be provided as an overlay on top of three-dimensional elements that the UID is controlling. This type of indicator could be used to indicate what edge of the workspace the UID is closest to as well as the tool that is affected. For example, the indicator could show the UID coming close to the top of the workspace boundary by a deformed two-dimensional line, or three-dimensional plane, placed over a three-dimensional graphical illustration of the tool.

Figure 19:
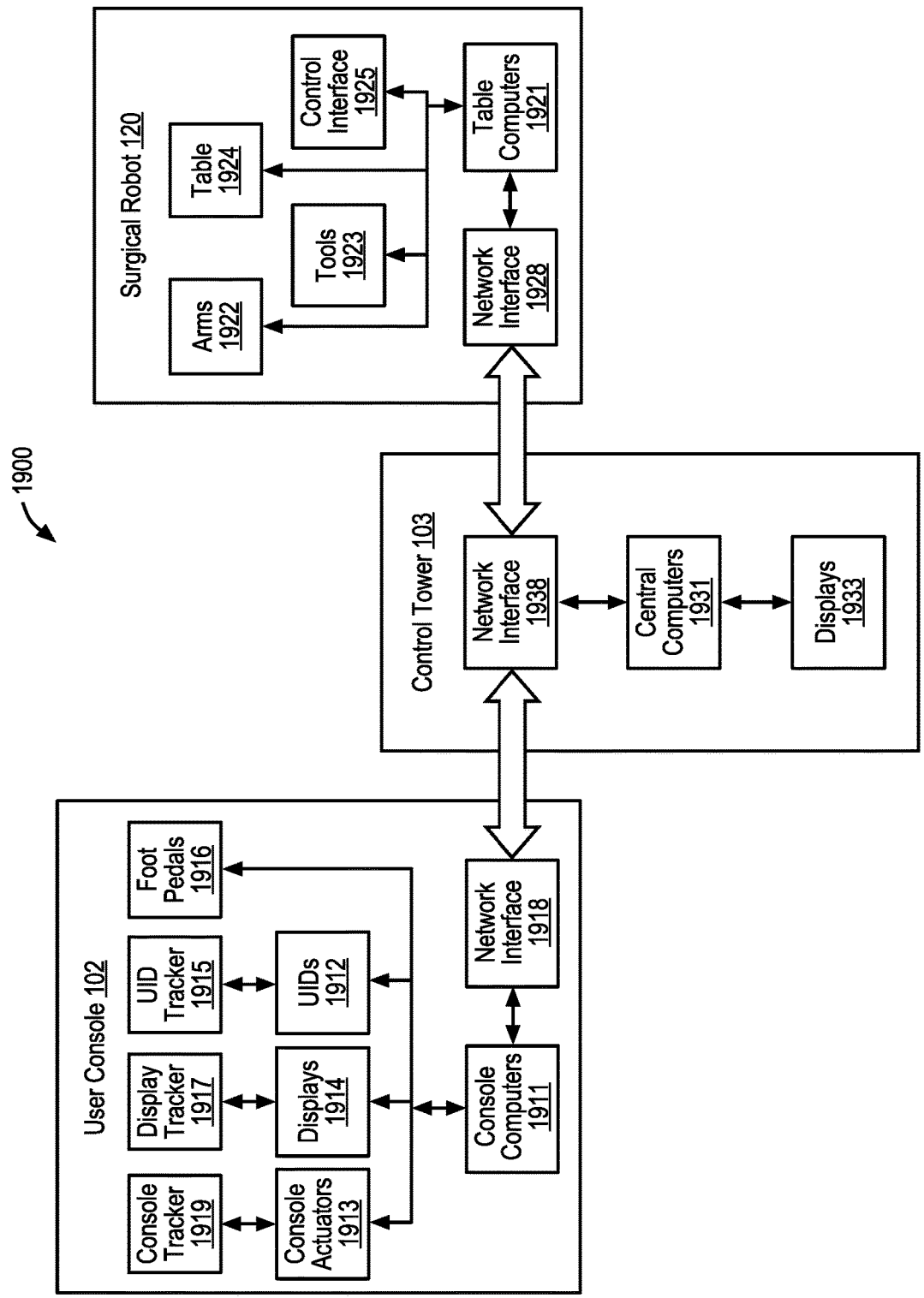
FIG. 19 is a block diagram of an exemplary processing operation of a surgical robotic system, in accordance with an embodiment.

FIG. 19 is a block diagram of a computer portion of a surgical robotic system, which is operable to implement the previously discussed operations, in accordance with an embodiment. The exemplary surgical robotic system 1900 may include a user console 102, a surgical robot 120, and a control tower 103. The surgical robotic system 1900 may include other or additional hardware components; thus, the diagram is provided by way of example and not a limitation to the system architecture.

As described above, the user console 102 may include console computers 1911, one or more UIDs 1912, console actuators 1913, displays 1914, foot pedals 1116, console computers 1911 and a network interface 1918. In addition, user console 102 may include a number of components, for example, a UID tracker(s) 1915, a display tracker(s) 1917 and a console tracker(s) 1919, for detecting various surgical conditions required for operation of the system (e.g., UID orientation, orientation of the surgeon relative to the display, orientation the console seat, etc.). It should further be understood that a user or surgeon sitting at the user console 102 can adjust ergonomic settings of the user console 102 manually, or the settings can be automatically adjusted according to user profile or preference. The manual and automatic adjustments may be achieved through driving the console actuators 1913 based on user input or stored configurations by the console computers 1911. The user may perform robot-assisted surgeries by controlling the surgical robot 120 using one or more master UIDs 1912 and foot pedals 1916. Positions and orientations of the UIDs 1912 are continuously tracked by the UID tracker 1915, and status changes are recorded by the console computers 1911 as user input and dispatched to the control tower 103 via the network interface 1918. Real-time surgical video of patient anatomy, instrumentation, and relevant software apps can be presented to the user on the high resolution 3D displays 1914 including open or immersive displays.

The user console 102 may be communicatively coupled to the control tower 103. The user console also provides additional features for improved ergonomics. For example, the user console may be an open architecture system including an open display, although an immersive display, in some cases, may be provided. Furthermore, a highly-adjustable seat for surgeons and master UIDs tracked through electromagnetic or optical trackers are included at the user console 102 for improved ergonomics.

The control tower 103 can be a mobile point-of-care cart housing touchscreen displays, computers that control the surgeon's robotically-assisted manipulation of instruments, safety systems, graphical user interface (GUI), light source, and video and graphics computers. As shown in FIG. 19, the control tower 103 may include central computers 1931 including at least a visualization computer, a control computer, and an auxiliary computer, various displays 1933 including a team display and a nurse display, and a network interface 1918 coupling the control tower 103 to both the user console 102 and the surgical robot 120. The control tower 103 may offer additional features for user convenience, such as the nurse display touchscreen, soft power and E-hold buttons, user-facing USB for video and still images, and electronic caster control interface. The auxiliary computer may also run a real-time Linux, providing logging/monitoring and interacting with cloud-based web services.

The surgical robot 120 may include an operating table 1924 with a plurality of integrated robotic arms 1922 that can be positioned over the target patient anatomy. A suite of compatible tools 1923 can be attached to or detached from the distal ends of the arms 1922, enabling the surgeon to perform various surgical procedures. The surgical robot 120 may also comprise control interface 1925 for manual or automated control of the arms 1922, table 1924, and tools 1923. The control interface can include items such as, but not limited to, remote controls, buttons, panels, and touchscreens. Other accessories such as trocars (sleeves, seal cartridge, and obturators) and drapes may also be needed to perform procedures with the system. In some variations, the plurality of the arms 1922 includes four arms mounted on both sides of the operating table 1924, with two arms on each side. For certain surgical procedures, an arm mounted on one side of the table can be positioned on the other side of the table by stretching out and crossing over under the table and arms mounted on the other side, resulting in a total of three arms positioned on the same side of the table 1924. The surgical tool can also comprise table computers 1921 and a network interface 1918, which can place the surgical robot 120 in communication with the control tower 103.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A method of determining a location of an interface device of a surgical robotic system within a surgical workspace using a virtual workspace, the method comprising:
   determining, by one or more processors communicatively coupled to the interface device, that a user is engaging with the interface device within a surgical workspace;
   in response to determining the user is engaging with the interface device,
      displaying a virtual interface device within a virtual workspace boundary, the virtual workspace boundary representing a workspace limit within which the interface device is operable to control a surgical robotic instrument in a teleoperation mode, wherein at least a portion of the virtual workspace boundary is operable to move in response to a movement of the interface device;
      determining, by the one or more processors, a location of the interface device relative to the surgical workspace based on a position of the virtual interface device relative to the virtual workspace boundary; and
      providing feedback when the position of the virtual interface device meets or exceeds the virtual workspace boundary.

2. The method of claim 1 wherein the virtual workspace boundary is a first virtual workspace boundary comprising a first three dimensional shape, and the method further comprises displaying a second virtual workspace boundary that represents a second workspace limit beyond which the interface device is inoperable to control the surgical robotic instrument in the teleoperation mode, the second virtual workspace boundary comprises a second three dimensional shape that encompasses the first three dimensional shape, and determining the location of the interface device further comprises determining a proximity of the portion of the first virtual workspace boundary relative to the second virtual workspace boundary.

3. The method of claim 2 wherein an area between the first three dimensional shape and the second three dimensional shape defines a warning zone that indicates the interface device is nearing the second workspace limit.

4. The method of claim 1 wherein the virtual workspace boundary comprises a cube shape.

5. The method of claim 4 wherein the portion of the virtual workspace boundary operable to move is a side wall of the cube shape.

6. The method of claim 1 wherein determining the location comprises:
   detecting that the portion of the virtual workspace boundary has moved, and the method further comprises:
   in response to the detecting, providing user feedback.

7. The method of claim 6, wherein the feedback comprises changing a visual characteristic of the virtual workspace boundary.

8. The method of claim 1 wherein the virtual workspace boundary is a first virtual workspace boundary, and determining the location comprises:
   detecting that the portion of the first virtual workspace boundary intersects with a second virtual workspace boundary that surrounds the first virtual workspace boundary, and the method further comprises:
   in response to the detecting, providing user feedback.

9. The method of claim 8, wherein the feedback comprises changing a visual characteristic of the first virtual workspace boundary or the second virtual workspace boundary.

10. The method of claim 8 wherein the feedback comprises a haptic feedback.

11. The method of claim 1 wherein the interface device is an ungrounded interface device.

12. A method of determining a location of an interface device of a surgical robotic system within a surgical workspace, the method comprising:
    determining, by one or more processors communicatively coupled to the surgical robotic system, whether a user is engaging with an interface device;
    in response to determining the user is engaging with the interface device, determining, by one or more processors communicatively coupled to the surgical robotic system, whether the interface device is within a warning zone of the surgical workspace; and
    in response to determining the interface device is within the warning zone, providing user feedback.

13. The method of claim 12 wherein the surgical workspace comprises a workspace limit beyond which the interface device is inoperable to control a surgical robotic instrument, and the warning zone comprises an area of the surgical workspace near the workspace limit.

14. The method of claim 12 wherein determining the interface device is within a warning zone comprises:
    providing a virtual three-dimensional boundary representing a boundary of the warning zone beyond which the interface device is inoperable to control a surgical robotic instrument; and
    determining a location of the interface device within the surgical workspace corresponds to an area within the virtual three-dimensional boundary.

15. The method of claim 12 wherein providing user feedback comprises providing the user with haptic feedback indicating the interface device is near a workspace limit of the surgical workspace.

16. The method of claim 12 wherein providing user feedback comprises providing the user with haptic feedback indicating the interface device has exceeded a workspace limit of the surgical workspace.

17. The method of claim 12 wherein the surgical workspace comprises a workspace limit defined by a plurality of sides, and providing user feedback comprises providing the user with information indicating which of the plurality of sides the interface device is closest to.

18. The method of claim 17 wherein the plurality of sides define a workspace limit having a three-dimensional shape.

19. The method of claim 12 wherein the interface device is a first interface device, and the surgical robotic system further comprises a second interface device, and providing user feedback comprises providing the user with information indicating whether the first interface device or the second interface device is in the warning zone.

20. The method of claim 19 wherein the surgical workspace comprises a three-dimensional shape and providing user feedback further comprises providing the user with information indicating which side of the three-dimensional shape the first interface device or the second interface device is closest to.

* * * * *